United States Patent
Hain et al.

(10) Patent No.: US 9,686,994 B2
(45) Date of Patent: Jun. 27, 2017

(54) USE OF ALS INHIBITOR HERBICIDES FOR CONTROL OF UNWANTED VEGETATION IN ALS INHIBITOR HERBICIDE TOLERANT BETA VULGARIS PLANTS

(71) Applicant: BAYER CROPSCIENCE AG, Monheim (DE)

(72) Inventors: Ruediger Hain, Frankfurt (DE); Gerhard Johann, Burscheid (DE)

(73) Assignee: BAYER CROPSCIENCE AG, Monheim (DE)

( * ) Notice: Subject to any disclaimer, the term of this patent is extended or adjusted under 35 U.S.C. 154(b) by 57 days.

(21) Appl. No.: 14/651,241

(22) PCT Filed: Dec. 10, 2013

(86) PCT No.: PCT/EP2013/075998
§ 371 (c)(1),
(2) Date: Jun. 11, 2015

(87) PCT Pub. No.: WO2014/090760
PCT Pub. Date: Jun. 19, 2014

(65) Prior Publication Data
US 2015/0313237 A1    Nov. 5, 2015

Related U.S. Application Data

(60) Provisional application No. 61/736,620, filed on Dec. 13, 2012.

(30) Foreign Application Priority Data

Dec. 13, 2012 (EP) .................................. 12196862

(51) Int. Cl.
| | | |
|---|---|---|
| A01N 47/36 | (2006.01) |
| A01N 43/40 | (2006.01) |
| A01N 43/48 | (2006.01) |
| A01N 43/653 | (2006.01) |
| A01N 43/66 | (2006.01) |
| A01N 43/50 | (2006.01) |
| A01N 43/54 | (2006.01) |
| A01N 47/38 | (2006.01) |
| A01N 43/90 | (2006.01) |
| A01N 43/52 | (2006.01) |
| A01N 61/00 | (2006.01) |
| A01N 25/00 | (2006.01) |
| A01N 25/32 | (2006.01) |
| C12N 15/82 | (2006.01) |

(52) U.S. Cl.
CPC ............ *A01N 47/36* (2013.01); *A01N 25/00* (2013.01); *A01N 25/32* (2013.01); *A01N 43/52* (2013.01); *A01N 43/90* (2013.01); *A01N 47/38* (2013.01); *A01N 61/00* (2013.01); *C12N 15/8278* (2013.01)

(58) Field of Classification Search
None
See application file for complete search history.

(56) References Cited

U.S. PATENT DOCUMENTS

| | | |
|---|---|---|
| 5,013,659 A | 5/1991 | Bedbrook et al. |
| 5,141,870 A | 8/1992 | Bedbrook et al. |
| 5,198,599 A | 3/1993 | Thill |
| 5,378,824 A | 1/1995 | Bedbrook et al. |
| 2010/0287641 A1 | 11/2010 | McElver et al. |
| 2013/0190179 A1 | 7/2013 | Hain et al. |
| 2013/0247253 A1 | 9/2013 | Hain et al. |

FOREIGN PATENT DOCUMENTS

| | | |
|---|---|---|
| EP | 0360750 A2 | 3/1990 |
| WO | 9802526 A1 | 1/1998 |
| WO | 9802527 A1 | 1/1998 |
| WO | 2008124495 A2 | 10/2008 |
| WO | 2009046334 A1 | 4/2009 |
| WO | 2012049266 A1 | 4/2012 |
| WO | 2012049268 A1 | 4/2012 |

OTHER PUBLICATIONS

International Search Report from corresponding PCT/EP2013/075998, mailed Mar. 21, 2014.
Beyer et al., "Sulfonylureas", Chapter 3, Agricultural Products Department, Wilmington, DE, 1988, pp. 117-189.
Chipman, "Biosynthesis of 2-aceto-2-hydroxy acids: acetolactate synthases and acetohydroxyacid synthases", Elsevier, Biochimica et Biophysica Acta 1385, 1998, pp. 401-419.
Chang et al., "Herbicide-resistant forms of Arabidopsis thaliana acetohydroxyacid synthase : characterization of the catalytic properties and sensitivity to inhibitors of four defined mutants", Biochem. J. (1998) 333, pp. 765-777 (Printed in Great Britain).
Saunders et al., "Monogenic Dominant Sulfonylurea Resistance in Sugarbeet from Somatic Cell Selection", Published in Crop Sci. 32: pp. 1357-1360, 1992.
Duggleby et al., "Structure and Properties of Acetohydroxyacid Synthase", The University of Queensland, Brisbane, Australia, 2004, pp. 251-274.

(Continued)

*Primary Examiner* — Alton Pryor
(74) *Attorney, Agent, or Firm* — McBee Moore Woodward Vanik IP LLC

(57) ABSTRACT

The present invention relates to the use of the ALS inhibitor herbicides for controlling unwanted vegetation in ALS inhibitor herbicide tolerant *Beta vulgaris* plants, more especially, present invention relates to the use of ALS inhibitor herbicides for control of unwanted vegetation in *Beta vulgaris*, preferably in sugar beet growing areas in which the *Beta vulgaris*, preferably sugar beet comprise mutations in the ALS gene where the tryptophan at position 569 in the encoded ALS enzyme is substituted by another amino acid (preferably by leucine), and a mutation in the ALS gene where the proline at position 188 in the encoded ALS enzyme is substituted by another amino acid (preferably by serine).

12 Claims, 1 Drawing Sheet

(56) References Cited

OTHER PUBLICATIONS

Duggleby et al., "Systematic characterization of mutations in yeast acetohydroxyacid synthase", Interpretation of herbicide-resistance date, Eur. J. Biochem. 270, pp. 2895-2904, 2003.
B. Ford-Lloyd, "Genetics and Breeding of Sugar Beet", Science Publishers, Inc., Enfield, New Hampshire, 2005, pp. 1-33.
Shimizu et al., "Acetolactate Synthase Inhibitors", Herbicide Classes in Development, Springer-Verlag Berlin Heidlberg 2002, pp. 1-41.
Jander et al., "Ethylmethanesulfonate Saturation Mutagenesis in Arabidopsis to Determine Frequency of Herbicide Resistance", Plant Physiology, Jan. 2003, vol. 131, pp. 139-146.
Duggleby et al., "Acetohydroxyacid Synthase", Journal of Biochemistry and Molecular Biology, vol. 33, No. 1, Jan. 1, 2000, pp. 1-36.
Pang et al., "Molecular Basis of Sulfonylurea Herbicide Inhibition of Acetohydroxyacid Synthase", The Journal of Biological Chemistry, vol. 278, No. 9, Issue of Feb. 28, 2003, pp. 7639-7644.
Jung et al., "Amino acid residues conferring herbicide resistance in tobacco acetohydroxy acid synthase", Biochemical Society, 2004, pp. 53-61, Printed in Great Britain.
Kleschick et al, "DE-498, a New Acetolactate Synthase Inhibiting Herbicide with Multicrop Selectivity", J. Agric. Food Chem. 1992, 40, pp. 1083-1085.
Hattori, "An acetohydroxy acid synthase mutant reveals a single site involved in multiple herbicide resistance", Mol Gen Genet, Springer Verlag 1995, pp. 419-425.
Tan et al., "Imidazolinone-tolerant crops: history, current status and future", Society of Chemical Industry, Pest Management Science, 2005, pp. 246-257, XP009058795.
Duggleby et al., "Structure and mechanism of inhibition of plant acetohydroxyacid synthase", Elsevier, ScienceDirect, Plant Physiology and Biochemistry 46, 2008, pp. 309-324.
Pontzen, "Propoxycarbazone-sodium (BAY MKH 6561): systemic properties and basis of selectivity in wheat", Pflanzenschutz-Nachrichten Bayer 55/2002, 1, pp. 37-52.
Shaner et al, Short Communication Imidazolinones "Potent Inhibitors of Acetohydroxyacid Synthase", Plant Physiol., 1984, pp. 545-546.
Shaner et al., "The Imadazolinone Herbicides", CRC Press, Boca Raton, FL, 1991, 3 pages.
Shimizu, "Action Mechanism of Pyrimidinyl Carboxy Herbicides", Life Science Research Institute, Kumiai Chemical Industry Co., Ltd., Ogasa-gun, Shizuoka 439, Japan, 1997, pp. 245-256.
Kolkman, "Acetohydroxyacid synthase mutations conferring resistance to imidazolinone or sulfonylurea herbicides in sunflower", Theor Appl Genet, 2004, pp. 1147-1159.
Umbarger, "Amino Acid Biosynthesis and its Regulation", Ann. Rev. Biochem., 1978, Department of Biological Sciences, Purdue University, West Lafayette, Indiana, pp. 533-606.
Tranel, "Resistance of weeds to ALS-inhibiting herbicides: what have we learned?", Weed Science 50, Nov.-Dec. 2002, pp. 700-712.
Stougaard et al, "Herbicide Resistant Mutants of Sugar Beet", 1990, J. Cell Biochem., Suppl. 14E, R249, p. 310- , XP001028988.
Sibony, Molecular basis for multiple resistance to acetolactate synthase-inhibiting herbicides and atrazine in Amaranthus blitoides (prostrate pigweed), Planta, 2003, Institute of Plant Science and Genetics, The Hebrew University of Jerusalem, Rehovot, Israel, pp. 1022-1027, XP002631640.
Yadav et al., "Single amino acid substitutions in the enzyme acetolactate synthase confer resistance to the herbicide sulfometruron methyl", Proc. Natl. Acad. Sci. USA, vol. 83, pp. 4418-4428, Jun. 1986, Genetics.

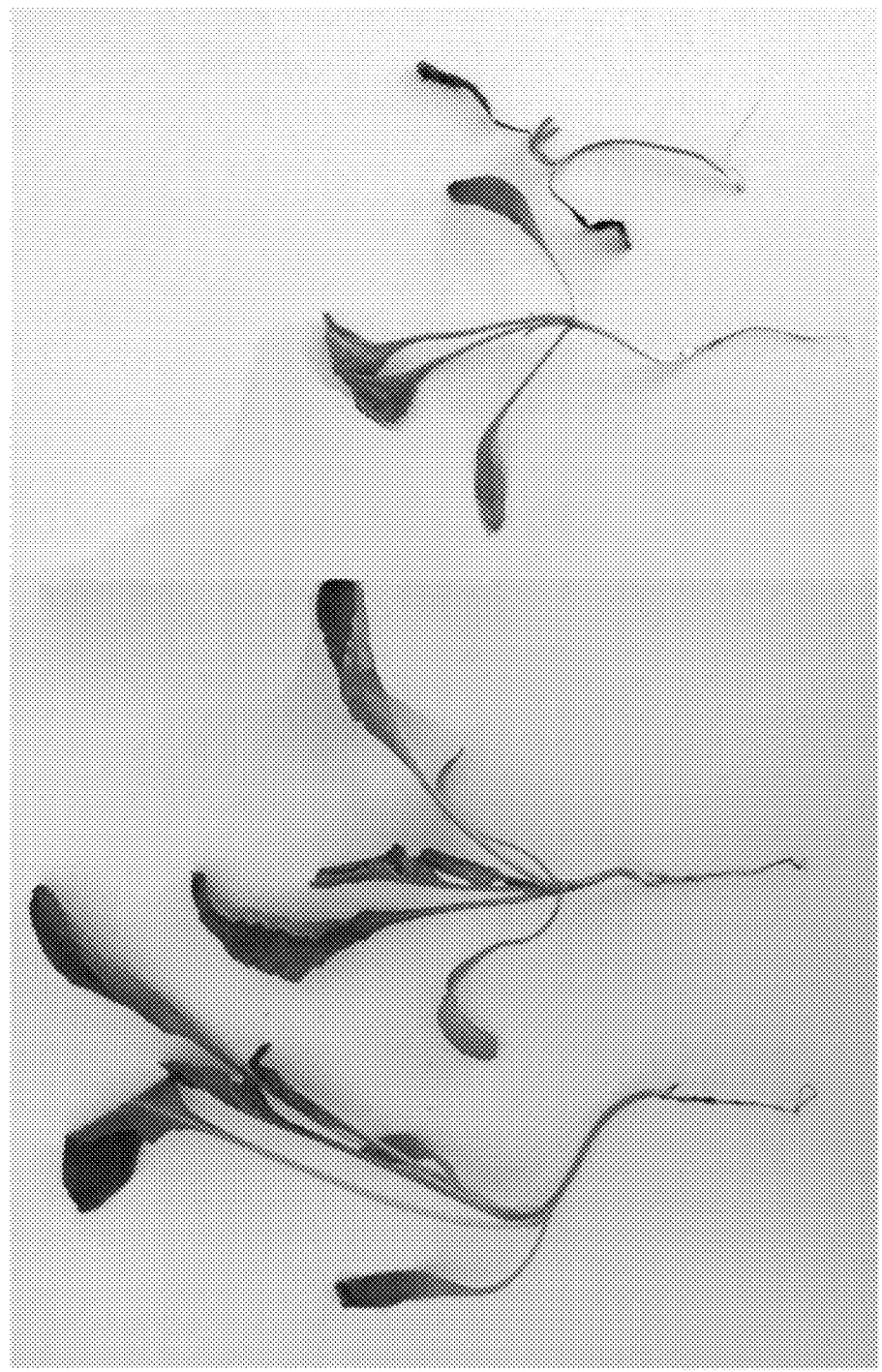

USE OF ALS INHIBITOR HERBICIDES FOR CONTROL OF UNWANTED VEGETATION IN ALS INHIBITOR HERBICIDE TOLERANT BETA VULGARIS PLANTS

CROSS REFERENCE TO RELATED APPLICATIONS

This application is a §371 National Stage Application of PCT/EP2013/075998, filed 10 Dec. 2013, which claims priority to EP 12196862.2, filed 13 Dec. 2012 and U.S. 61/736,620, filed 13 Dec. 2012.

BACKGROUND

Field of the Invention

The present invention relates to the technical field of crop protection by using ALS (acetolactate synthase; also known as AHAS (acetohydroxyacid synthase; EC 2.2.1.6; formerly EC 4.1.3.18)) inhibitor herbicides against unwanted vegetation in areas of growing Beta vulgaris plants, preferably sugar beet, that are tolerant against ALS inhibitor herbicides by comprising mutations in the endogenous ALS gene thereby encoding an ALS polypeptide having an amino acid that is different from the naturally occurring tryptophan (i.e. the tryptophan of the wild-type ALS protein) at position 569 and having an amino acid that is different from the naturally occurring proline (i.e. the proline of the wild-type ALS protein) at position 188.

Description of Related Art

Thus, the mutated sugar beet plants used in the context of the present invention comprise mutations in the ALS gene where the tryptophan at position 569 in the encoded ALS enzyme (corresponding to position 574 in the *Arabidopsis thaliana* ALS enzyme) is substituted by another amino acid (preferably by leucine), and a mutation in the ALS gene where the proline at position 188 in the encoded ALS enzyme (corresponding to position 197 in *Arabidopsis thaliana* ALS enzyme) is substituted by another amino acid (preferably by serine).

Cultivated forms of Beta vulgaris (as defined in Ford-Lloyd (2005) Sources of genetic variation, Genus Beta. In: Biancardi E, Campbell L G, Skaracis G N, De Biaggi M (eds) Genetics and Breeding of Sugar Beet. Science Publishers, Enfield (NH), USA, pp 25-33) are important agricultural crops in temperate and subtropical regions. For example, about 20% of the world sugar production is based on sugar beet. Because beet seedlings and juvenile plants during their first 6-8 weeks of their life are susceptible for strong competition caused by fast growing weeds, which outcompete the young crop plants, reliable weed control measures are imperative in these crop areas.

Since more than 40 years, herbicides are the preferred tools to control weeds in sugar beet (*Beta vulgaris* subsp. *vulgaris* var *altissima*). The products used for this purpose, namely phenmedipham, desmediphan, ethofumesate, and metamitron allow to suppress weeds in sugar beet fields without damaging the crop. Nevertheless, under adverse environmental conditions the efficacy of these products leaves room for improvements, especially if noxious weeds like *Chenopodium album, Amaranthus retroflexus* and/or *Fallopia convolvulus* germinate over an extended period of time.

The ALS/AHAS enzyme is present in bacteria, fungi, and plants and from various organisms protein isolates have been obtained and their corresponding amino acid/nucleic acid sequences as well as their biochemical characteristics have been determined/characterized (for review, see at Umbarger, H. E., Annu. Rev. Biochem. (1978), 47, 533-606; Chiman, D. M. et al., Biochim Biophys. Acta (1998), 1385, 401-419; Duggleby, R. G., and Pang, S. S., J. Biochem. Mol. Biol. (2000), 33, 1-36; Duggleby, R. G. (Structure and Properties of Acetohydroxyacid Synthase in Thiamine: Catalytic Mechanisms in Normal and Disease States, Vol 11, Marcel Dekker, New York, 2004, 251-274)

The use of herbicidal compounds belonging to the class of ALS inhibitors, like (a) sulfonylurea herbicides (Beyer E. M et al. (1988), Sulfonylureas in Herbicides: Chemistry, Degradation, and Mode of Action; Marcel Dekker, New York, 1988, 117-189), (b) sulfonylaminocarbonyltriazolinone herbicides (Pontzen, R., Pflanz.-Nachrichten Bayer, 2002, 55, 37-52), (c) imidazolinone herbicides (Shaner, D. L., et al., Plant Physiol., 1984, 76, 545-546; Shaner, D. L., and O'Connor, S. L. (Eds.) The Imidazolinone Herbicides, CRC Press, Boca Raton, Fla., 1991), (d) triazolopyrimidine herbicides (Kleschick, W. A. et al., Agric. Food Chem., 1992, 40, 1083-1085), and (e) pyrimidinyl(thio)benzoate herbicides (Shimizu, T. J., Pestic. Sci., 1997, 22, 245-256; Shimizu, T. et al., Acetolactate Syntehase Inhibitors in Herbicide Classes in Development, Boger, P., Wakabayashi. K., Hirai, K., (Eds.), Springer Verlag, Berlin, 2002, 1-41) for the control of unwanted vegetation in various crop cultures is well known in agriculture.

A broad variety of ALS/AHAS inhibitor herbicides enable a farmer to control a wide range of weed species independently of their growth stages, but these highly efficient herbicides cannot be used in Beta vulgaris, preferably sugar beet, because Beta vulgaris, especially conventional sugar beet plants/commercial sugar beet varieties are highly susceptible against/affected by these ALS inhibitor herbicides. Nevertheless, these ALS inhibitor herbicides show an excellent herbicidal activity against broadleaf and grass weed species. The first herbicides based on ALS inhibitors were developed for their use in agriculture already 30 years ago. Nowadays, active ingredients of this class exhibit a strong weed control and are widely used in maize and cereals as well as in dicot crops, except Beta vulgaris, preferably sugar beet.

By now, there is only one commercially available product based on a sulfonylurea herbicide, i.e. Debut® (component (A) 50% triflusulfuron-methyl+component (B) a specific formulation compound, i.e. a specific adjuvant) which can be used in sugar beet in post emergent application, but it requires the application at a very early leaf stage of the weeds to be treated and also show severe gaps in the treatment of serious weeds growing in sugar beet plantings. This sulfonylurea is not tolerated by but degraded in the sugar beet plants.

Another, more reliable and more flexible way to obtain Beta vulgaris, preferably sugar beet plants that stand an ALS inhibitor herbicide treatment is to generate mutants that are sufficiently tolerant to agronomically useful/necessary quantities of ALS inhibitor herbicides in order to control serious unwanted vegetation in Beta vulgaris, preferably sugar beet plantings.

Since ALS inhibitor herbicides were introduced into agriculture it was observed that susceptible plant species, including naturally occurring weeds, occasionally develop spontaneous tolerance to this class of herbicides. Single base pair substitutions at specific sites of the ALS gene usually lead to more or less resistant ALS enzyme variants which show different levels of inhibition by the ALS inhibitor herbicides.

Plants conferring mutant ALS alleles therefore show different levels of tolerance to ALS inhibitor herbicides, depending on the chemical structure of the ALS inhibitor herbicide and the site of the point mutation(s) in the ALS gene and the hereby encoded ALS protein.

Several mutants (naturally occurring in weeds but also artificially induced in crops by either mutation or transgenic approaches) of the ALS conferring tolerance to one or more chemicals defined under the above given ALS inhibitor herbicide classes/groups are known at various parts of the enzyme (i.e. in the α-, β-, and γ-domain of the ALS h are known and have been identified in various organisms, including plants (U.S. Pat. No. 5,378,824; Duggleby, R. G. et al., (2008), Plant Physiol. and Biochem., pp 309-324; Siyuan, T. et al. (2005), Pest Management Sci., 61, pp 246-257; Jung, S. (2004) Biochem J., pp 53-61; Kolkman, J. M. (2004), Theor. Appl. Genet., 109, pp 1147-1159; Duggleby, R. G. et al (2003), Eur. J. Biochem., 270, pp 2895-2904; Pang, S. S., et al. (2003), J. Biol. Chem., pp 7639-7644); Yadav, N. et al., (1986), Proc. Natl. Acad. Sci., 83, pp 4418-4422), Jander G. et al. (2003), Plant Physiol., 131, pp. 139-146); Tranel, P. J., and Wright, T. R. (2002), Weed Science, 50, pp 700-712); Chang, A. K., and Duggleby, R. G. (1998), Biochem J., 333, pp. 765-777).

Crop plants conferring mutant ALS alleles do show different levels of tolerance to ALS inhibitor herbicides, depending on the chemical structure of the ALS inhibitor herbicide and the site of the point mutation in the ALS gene.

For example, Hattori et al. (1995), Mol. Gen. Genet. 246: 419-425, describes a single mutation in the Trp 557 codon in a *Brassica napus* cell line (according to the numbering of the *Arabidopsis thaliana* sequence that is used in the literature in order to compare all ALS/AHAS mutants this refers to position "574")—which equals position 569 of the sugar beet ALS polypeptide sequence. These authors observed resistance to several members of sub-classes of ALS inhibitor herbicides, like sulfonylureas, imidazolinones and triazolopyrimidines.

EP-A-0360750 describes the production of ALS inhibitor herbicide tolerant plants by producing an increased amount of the attacked ALS inside the plant. Such plants show an increased tolerance against certain sulfonyureas, like chlorsulfuron, sulfometuron-methyl, and triasulfuron.

U.S. Pat. No. 5,198,599 describes sulfonylurea and imidazolinone tolerant plants that have been obtained via a selection process and which show a tolerance against chlorsulfuron, bensulfuron, chlorimuron, thifensulfuron and sulfometuron.

Furthermore, U.S. Pat. No. 5,013,659, U.S. Pat. No. 5,141,870, and U.S. Pat. No. 5,378,824 describe the production of transgenic sugar beet plants by introducing a modified yeast ALS gene into such sugar beet plants.

In addition, Saunders et al. (Crop Science, 1992, 32, 1357-1360) disclose sulfonylurea tolerant sugar beet plants that were obtained via somaclonal cell selection but these authors neither showed up any biological data concerning the level of tolerance of such plants against ALS inhibitor herbicide treatment nor did they demonstrate genetically stable mutants obtained from cultures in which these mutations have been generated.

Tan et al. report in Pest Manag. Sci. 2005, 61, 246-257 on weed control in certain imidazolinone-tolerant crops.

Stougaard et al. (1990), J. Cell Biochem., Suppl. 14E, 310 describe the isolation of ALS mutants in a tetraploid sugar beet cell culture. Two different ALS genes (ALS I and ALS II) were isolated which differed at amino acid position 37 only. Mutant 1 contained in its ALS I gene 2 mutations, while mutant 2 contained 3 mutations in its ALS II gene. After the mutations were separated to resolve which mutation would confer resistance against an ALS inhibitor, it was revealed that ALS synthesized from a recombinant *E. coli* was herbicide resistant if it contained a point mutation in the Trp 574 codon (according to the numbering of the *Arabidopsis thaliana* sequence that is used in the literature in order to compare all ALS mutants)—which equals position 569 of the beet ALS amino acid sequence, leading to a replacement of the amino acid "Trp" by the amino acid "Leu". Stougaard et al did not show in sugar beet that the mutation at position 569 of any of the sugar beet ALS genes is sufficient in order to obtain an agronomically acceptable level of tolerance to ALS inhibitor herbicides. Moreover, Stougaard et al did not regenerate or handle sugar beet plants comprising a mutation, including Trp→Leu mutation at position 569 of sugar beet ALS.

Knowing this, Stougaard et al. constructed plant transformation vectors containing different ALS genes for use in plant transformation. However, up to now, no further data—especially not concerning the effects of the application of ALS inhibitor herbicides to plants and/or agricultural areas comprising this mutation in *Beta vulgaris* plants have been disclosed by these or other authors either in genetically engineered or mutant plants over more than 20 years, thereafter.

Additionally, beet mutants were described conferring a point mutation in the Ala 122 codon which led to a certain tolerance to the ALS inhibitor herbicide subclass of imidazolinones (WO 98/02526) but which is not sufficient for weed control in agricultural application schemes. No cross-tolerance to other ALS inhibitor herbicide classes was described by employing this mutant. Furthermore, beet plants conferring a second point mutation in the Pro 197 codon showed a moderate tolerance to ALS inhibitor herbicides belonging to members of the subclass of sulfonylurea herbicides. Also double mutants of these two were described (WO 98/02527). However, none of these mutants were used for the market introduction of beet varieties because the level of herbicide tolerance to ALS inhibitor herbicides was not sufficiently high in these mutants to be exploited agronomically.

WO 2012/049268 discloses a method for the manufacture of sugar beet plant resistant to several ALS inhibitors, including to foramsulfuron, which comprises the steps of exposing to foramsulfuron calli obtained from explants of *B. vulgaris*, and regenerating plants from the few spontaneous mutants that can grow in the presence of this herbicide. Said method yielded plants having a mutation in the ALS gene, where the tryptophan at position 569 of the encoded ALS enzyme (corresponding to the 574 position of the *Arabidopsis thaliana* ALS enzyme) is substituted by a leucine. WO 2012/049266 relates to the use of ALS inhibitor herbicides for control of unwanted vegetation in ALS inhibitor herbicide tolerant *Beta vulgaris* plants having a mutation in the ALS gene, where the tryptophan at position 569 of the encoded ALS enzyme.

WO 2008/124495 discloses ALS double and triple mutants. According to WO 2009/046334, specific mutations in the ALS gene were provided. However, agronomically exploitable *Beta vulgaris* mutants containing such mutations according to WO 2009/046334 and also showing a sufficient tolerance to any kind of ALS inhibitor herbicides of various ALS inhibitor herbicide classes have not been obtained/described by now.

All these sugar beet mutants do not show a reliable tolerance and/or do not show satisfactory tolerance against various classes of the ALS inhibitor herbicides, and—even worse—they do not show a tolerance level that is sufficient and useful at agronomic application rates against any kind of ALS inhibitor herbicides.

As it relates to the compounds known acting as ALS inhibitor herbicides, these can be grouped in several classes.

Compounds from the group of the (sulfon)amides are already known as herbicidally active compounds for controlling unwanted vegetation; see, for example, EP 239414, U.S. Pat. No. 4,288,244, DE 3303388, U.S. Pat. No. 5,457, 085, U.S. Pat. No. 3,120,434, U.S. Pat. No. 3,480,671, EP 206251, EP 205271, U.S. Pat. No. 2,556,664, U.S. Pat. No. 3,534,098, EP 053011, U.S. Pat. No. 4,385,927, EP 348737, DE 2822155, U.S. Pat. No. 3,894,078, GB 869169, EP 447004, DE 1039779, HU 176582, U.S. Pat. No. 3,442,945, DE 2305495, DE 2648008, DE 2328340, DE 1014380, HU 53483, U.S. Pat. No. 4,802,907, GB 1040541, U.S. Pat. No. 2,903,478, U.S. Pat. No. 3,177,061, U.S. Pat. No. 2,695,225, DE 1567151, GB 574995, DE 1031571, U.S. Pat. No. 3,175,897, JP 1098331, U.S. Pat. No. 2,913,327, WO 83/00329, JP 80127302, DE 1300947, DE 2135768, U.S. Pat. No. 3,175,887, U.S. Pat. No. 3,836,524, JP 85067463, U.S. Pat. No. 3,582,314, U.S. Pat. No. 5,333,0821, EP 131258, U.S. Pat. No. 4,746,353, U.S. Pat. No. 4,420,325, U.S. Pat. No. 4,394,506, U.S. Pat. No. 4,127,405, U.S. Pat. No. 4,479,821, U.S. Pat. No. 5,009,699, EP 136061, EP 324569, EP 184385, WO 02/30921, WO 92/15576, WO 95/29899, U.S. Pat. No. 4,668,277, EP 305939, WO 96/41537, WO 95/10507, EP 007677, CN 01080116, U.S. Pat. No. 4,789,393, EP 971902, U.S. Pat. No. 5,209,771, EP 084020, EP 120814, EP 087780, WO 88/04297, EP 5828924, WO 02/36595, U.S. Pat. No. 5,476,936, WO 2009/053058 and the literature cited in the publications mentioned above.

Compounds from the group of the imidazolinones are already known as herbicidally active compounds for controlling unwanted vegetation; see, for example Proc. South. Weed Sci. Soc. 1992. 45, 341, Proc. South. Weed Sci. Soc. Annu. Mtg. 36th, 1983, 29, Weed Sci. Soc. Annu. Mtg. 36th, 1983, 90-91, Weed Sci. Soc. Mtg., 1984, 18, Modern Agrochemicals, 2004, 14-15.

Compounds from the group of the pyrimidinyl(thio)benzoates are already known as herbicidally active compounds for controlling unwanted vegetation; see, for example U.S. Pat. No. 4,906,285, EP 658549, U.S. Pat. No. 5,118,339, WO 91/05781, U.S. Pat. No. 4,932,999, and EP 315889.

Compounds from the group of the sulfonanilides are already known as herbicidally active compounds for controlling unwanted vegetation; see, for example WO 93/09099, WO 2006/008159, and WO 2005/096818.

All publications and patents cited in this disclosure are incorporated by reference in their entirety. To the extent the material incorporated by reference contradicts or is inconsistent with this specification, the specification will supersede any such material.

SUMMARY

In view of the fact that, for example, sugar beet accounts for about 20% of the world sugar production, it would be highly desirable to have available a weed control system that enables the efficient control of highly potent and serious weeds. It would thus be highly desirable to use one or more ALS inhibitor herbicides for control of unwanted vegetation in *Beta vulgaris* plants, preferably sugar beet plants which are tolerant to such ALS inhibitor herbicides.

This problem was solved according to present invention.

The present invention relates to the use of one or more ALS inhibitor herbicide(s) belonging to one or various ALS inhibitor herbicide class(es) for controlling unwanted vegetation in *Beta vulgaris*, preferably in sugar beet growing areas in which the *Beta vulgaris* plant, preferably a sugar beet plant, comprises a mutation of tryptophan at position 569 in the ALS enzyme and a mutation of proline at position 188 in the ALS enzyme, as well as optionally one or several further mutations, preferably one or several further mutations in the ALS gene, preferably a mutation causing a further amino acid substitution in the ALS gene.

BRIEF DESCRIPTION OF THE DRAWINGS

FIG. 1 depicts embodiments of disclosure described herein.

DETAILED DESCRIPTION OF A PREFERRED EMBODIMENT

Seeds of sugar beet plants comprising such mutations and which are preferably employed according to present invention have been deposited with the NCIMB, Aberdeen, UK, under Number NCIMB 42050 on Sep. 7, 2012 (Bayer CropScience AG being co-depositor).

More preferably, the present invention relates to the use of one or more ALS inhibitor herbicide(s) in the above mentioned mutated *Beta vulgaris* plants, preferably in the above described mutated sugar beet plants, wherein the ALS inhibitor herbicide(s) belong to:

the group of the (sulfon)amides (group (A)) consisting of:
  the subgroup (A1) of the sulfonylureas, consisting of:
    amidosulfuron [CAS RN 120923-37-7] (=A1-1);
    azimsulfuron [CAS RN 120162-55-2] (=A1-2);
    bensulfuron-methyl [CAS RN 83055-99-6] (=A1-3);
    chlorimuron-ethyl [CAS RN 90982-32-4] (=A1-4);
    chlorsulfuron [CAS RN 64902-72-3] (=A1-5);
    cinosulfuron [CAS RN 94593-91-6] (=A1-6);
    cyclosulfamuron [CAS RN 136849-15-5] (=A1-7);
    ethametsulfuron-methyl [CAS RN 97780-06-8] (=A1-8);
    ethoxysulfuron [CAS RN 126801-58-9] (=A1-9);
    flazasulfuron [CAS RN 104040-78-0] (=A1-10);
    flucetosulfuron [CAS RN 412928-75-7] (=A1-11);
    flupyrsulfuron-methyl-sodium [CAS RN 144740-54-5] (=A1-12);
    foramsulfuron [CAS RN 173159-57-4] (=A1-13);
    halosulfuron-methyl [CAS RN 100784-20-1] (=A1-14);
    imazosulfuron [CAS RN 122548-33-8] (=A1-15);
    iodosulfuron-methyl-sodium [CAS RN 144550-36-7] (=A1-16);
    mesosulfuron-methyl [CAS RN 208465-21-8] (=A1-17);
    metsulfuron-methyl [CAS RN 74223-64-6] (=A1-18);
    monosulfuron [CAS RN 155860-63-2] (=A1-19);
    nicosulfuron [CAS RN 111991-09-4] (=A1-20);
    orthosulfamuron [CAS RN 213464-77-8] (=A1-21);
    oxasulfuron [CAS RN 144651-06-9] (=A1-22);
    primisulfuron-methyl [CAS RN 86209-51-0] (=A1-23);
    prosulfuron [CAS RN 94125-34-5] (=A1-24);
    pyrazosulfuron-ethyl [CAS RN 93697-74-6] (=A1-25);
    rimsulfuron [CAS RN 122931-48-0] (=A1-26);

sulfometuron-methyl [CAS RN 74222-97-2] (=A1-27);
sulfosulfuron [CAS RN 141776-32-1] (=A1-28);
thifensulfuron-methyl [CAS RN 79277-27-3] (=A1-29);
triasulfuron [CAS RN 82097-50-5] (=A1-30);
tribenuron-methyl [CAS RN 101200-48-0] (=A1-31);
trifloxysulfuron [CAS RN 145099-21-4] (sodium) (=A1-32);
triflusulfuron-methyl [CAS RN 126535-15-7] (=A1-33);
tritosulfuron [CAS RN 142469-14-5] (=A1-34);
NC-330 [CAS RN 104770-29-8] (=A1-35);
NC-620 [CAS RN 868680-84-6] (=A1-36);
TH-547 [CAS RN 570415-88-2] (=A1-37);
monosulfuron-methyl [CAS RN 175076-90-1] (=A1-38);
2-iodo-N-[(4-methoxy-6-methyl-1,3,5-triazinyl)carbamoyl]benzene-sulfonamide (=A1-39);
a compound of the general formula (I)

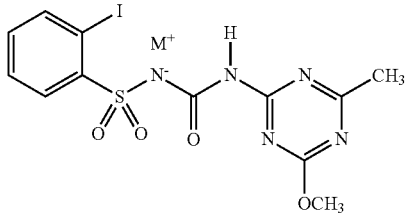

(I)

where M+ denotes the respective salt of the compound (I), i.e.

its lithium salt (=A1-40); its sodium salt (=A1-41); its potassium salt
(=A1-42); its magnesium salt (=A1-43); its calcium (=A1-44); its ammonium salt (=A1-45); its methylammonium salt (=A1-46); its dimethylammonium salt (=A1-47); its tetramethylammonium salt
(=A1-48); its ethylammonium salt (=A1-49); its diethylammonium salt (=A1-50); its tetraethylammonium salt (=A1-51); its propylammonium salt (=A1-52); its tetrapropylammonium salt (=A1-53); its isopropylammonium salt (=A1-54); its diisopropylammonium salt
(=A1-55); its butylammonium salt (=A1-56); its tetrabutylammonium salt (=A1-57); its (2-hydroxyeth-1-yl)ammonium salt (=A1-58); its bis-N,N-(2-hydroxyeth-1-yl)ammonium salt (=A1-59); its tris-N,N,N-(2-hydroxyeth-1-yl)ammonium salt (=A1-60); its 1-phenylethylammonium salt (=A1-61); its 2-phenylethylammonium salt (=A1-62); its trimethylsulfonium salt (=A1-63); its trimethyloxonium salt (=A1-64); its pyridinium salt
(=A1-65); its 2-methylpyridinium salt (=A1-66); its 4-methylpyridinium salt (=A1-67); its 2,4-dimethylpyridinium salt
(=A1-68); its 2,6-dimethylpyridinium salt (=A1-69); its piperidinium salt (=A1-70); its imidazolium salt (=A1-71); its morpholinium salt
(=A1-72); its 1,5-diazabicyclo[4.3.0]non-7-enium salt (=A1-73); its 1,8-diazabicylco[5.4.0]undec-7-enium salt (=A1-74);
or a compound of the formula (II) or salts thereof

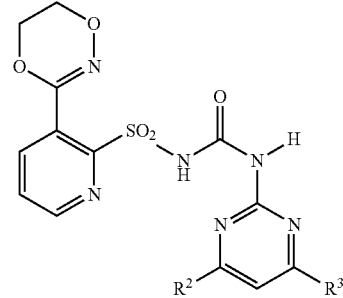

(II)

with R², and R³ having the meaning as defined in the below table

| Compound | R² | R³ |
|---|---|---|
| A1-75 | OCH₃ | OC₂H₅ |
| A1-76 | OCH₃ | CH₃ |
| A1-77 | OCH₃ | C₂H₅ |
| A1-78 | OCH₃ | CF₃ |
| A1-79 | OCH₃ | OCF₂H |
| A1-80 | OCH₃ | NHCH₃ |
| A1-81 | OCH₃ | N(CH₃)₂ |
| A1-82 | OCH₃ | Cl |
| A1-83 | OCH₃ | OCH₃ |
| A1-84 | OC₂H₅ | OC₂H₅ |
| A1-85 | OC₂H₅ | CH₃ |
| A1-86 | OC₂H₅ | C₂H₅ | or the compound of formula (III) (=A1-87), i.e. the sodium salt of compound (A1-83)

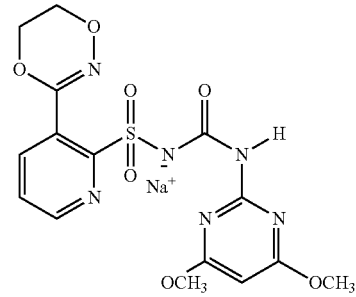

(III)

or the compound of formula (IV) (=A1-88), i.e. the sodium salt of compound (A1-82)

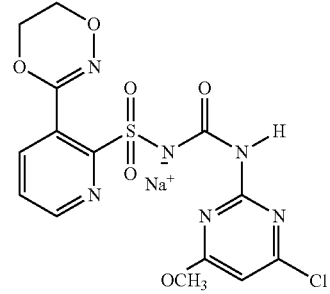

(IV)

the subgroup of the sulfonylaminocarbonyltriazolinones (subgroup ((A2)), consisting of:

flucarbazone-sodium [CAS RN 181274-17-9] (=A2-1);

propoxycarbazone-sodium [CAS RN 181274-15-7] (=A2-2);

thiencarbazone-methyl [CAS RN 317815-83-1] (=A2-3);

the subgroup of the triazolopyrimidines (subgroup (A3)), consisting of:

cloransulam-methyl [147150-35-4] (=A3-1);

diclosulam [CAS RN 145701-21-9] (=A3-2);

florasulam [CAS RN 145701-23-1] (=A3-3);

flumetsulam [CAS RN 98967-40-9] (=A3-4);

metosulam [CAS RN 139528-85-1] (=A3-5);

penoxsulam [CAS RN 219714-96-2] (=A3-6);

pyroxsulam [CAS RN 422556-08-9] (=A3-7);

the subgroup of the sulfonanilides (subgroup (A4)), consisting of:

compounds or salts thereof from the group described by the general formula (I):

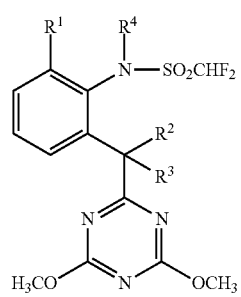

(V)

in which $R^1$ is halogen, preferably fluorine or chlorine, $R^2$ is hydrogen and $R^3$ is hydroxyl Or $R^2$ and $R^3$ together with the carbon atom to which they are attached are a carbonyl group C=O and $R^4$ is hydrogen or methyl;

and more especially compounds of the below given chemical structure (A4-1) to (A4-8)

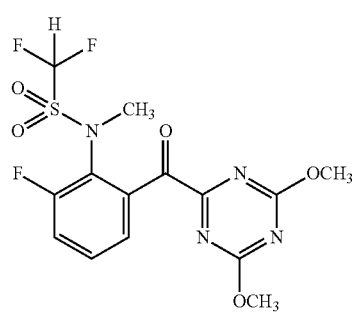

(A4-1)

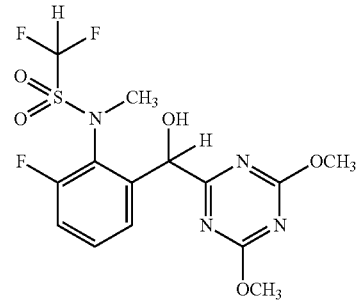

(A4-2)

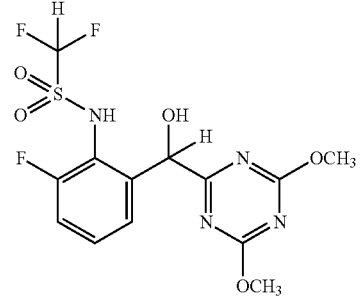

(A4-3)

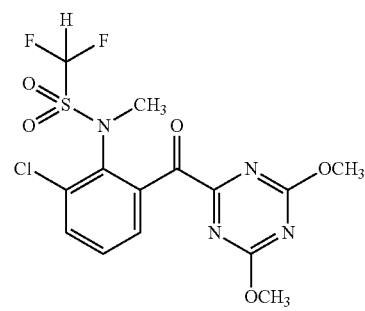

(A4-4)

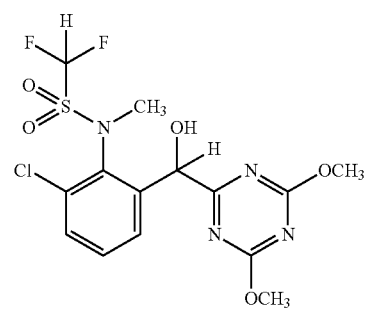

(A4-5)

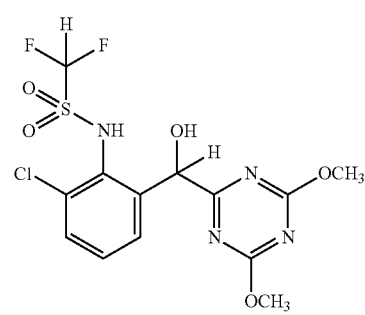

(A4-6)

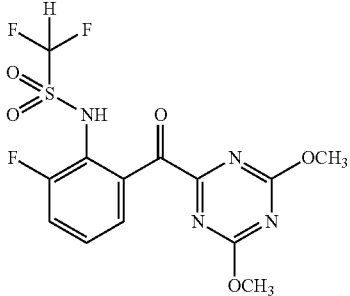

(A4-7)

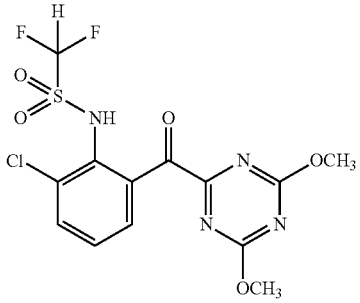

(A4-8)

the group of the imidazolinones (group (B1)), consisting of:
imazamethabenzmethyl [CAS RN 81405-85-8] (=B1-1);
imazamox [CAS RN 114311-32-9] (=B1-2);
imazapic [CAS RN 104098-48-8] (=B1-3);
imazapyr [CAS RN 81334-34-1] (=B1-4);
imazaquin [CAS RN 81335-37-7] (=B1-5);
imazethapyr [CAS RN 81335-77-5] (=B1-6);
SYP-298 [CAS RN 557064-77-4] (=B1-7);
SYP-300 [CAS RN 374718-10-2] (=B1-8).
the group of the pyrimidinyl(thio)benzoates (group (C)), consisting of:
the subgroup of the pyrimidinyloxybenzoeacids (subgroup (C1)) consisting of:
bispyribac-sodium [CAS RN 125401-92-5] (=C1-1);
pyribenzoxim [CAS RN 168088-61-7] (=C1-2);
pyriminobac-methyl [CAS RN 136191-64-5] (=C1-3);
pyribambenz-isopropyl [CAS RN 420138-41-6] (=C1-4);
pyribambenz-propyl [CAS RN 420138-40-5] (=C1-5);
the subgroup of the pyrimidinylthiobenzoeacids (subgroup (C2)), consisting of:
pyriftalid [CAS RN 135186-78-6] (=C2-1);
pyrithiobac-sodium [CAS RN 123343-16-8] (=C2-2).

In this context, "tolerance" or "tolerant" means that the application of one or more ALS inhibitor herbicide(s) belonging to any of the above defined groups (A), (B), (C) does not show any apparent effect(s) concerning the physiological functions/phytotoxicity when applied to the respective *Beta vulgaris* plant, especially sugar beet containing an ALS polypeptide comprising mutations at positions 569 and 188 and whereas the application of the same amount of the respective ALS inhibitor herbicide(s) on non-tolerant *Beta vulgaris* plants leads to significant negative effects concerning plant growth, its physiological functions or shows phytotoxic symptoms. Quality and quantity of the observed effects may depend on the chemical composition of the respective ALS inhibitor herbicide(s) applied, dose rate and timing of the application as well growth conditions/stage of the treated plants.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein.

Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. The word "comprise" and its variations on the one side and the word "contain" and its analogous variations on the other side can be used interchangeably throughout this specification and the corresponding claims without a preference given to any of them.

When used herein, the term "transgenic" or "genetically modified" means that a gene—which can be of the same or a different species—has been introduced via an appropriate biological carrier, like *Agrobacterium tumefaciens* or by any other physical means, like protoplast transformation or particle bombardment, into a plant and which gene is able to be expressed in the new host environment, namely the genetically modified organism (GMO).

In accordance to the before definition, the term "non-transgenic" or "non-genetically modified" means exactly the contrary, i.e. that no introduction of the respective gene has occurred via an appropriate biological carrier or by any other physical means. However, a mutated gene can be transferred through pollination, either naturally or via a breeding process to produce another non-transgenic plant concerning this specific gene.

An "endogenous" gene means a gene of a plant which has not been introduced into the plant by genetic engineering techniques.

An "amino acid different from tryptophan" (indicated by "Trp" in the three letter code or "W" in the equivalently used one letter code) includes any naturally-occurring amino acid different from tryptophan. These naturally-occurring amino acids include alanine (A), arginine (R), asparagine (N), aspartate (D), cysteine (C), glutamine (Q), glutamate (E), glycine (G), histidine (H), isoleucine (I), leucine (L), lysine (K), methionine (M), phenylalanine (F), proline (P), serine (S), threonine (T), tyrosine (Y) or valine (V).

However, preferably, the amino acid different from tryptophan (belonging to the group of neutral-polar amino acids) at position 569 of the ALS protein is an amino acid with physico-chemical properties different from tryptophan, i.e. belonging to any of the amino acids showing neutral-nonpolar, acidic, or basic properties. More preferably, the amino acid different from tryptophan is selected from the group consisting of alanine, glycine, isoleucine, leucine, methionine, phenylalanine, proline, valine, and arginine. Even more preferably, said amino acid is a neutral-nonpolar amino acid such as alanine, glycine, isoleucine, leucine, methionine, phenylalanine, proline or valine. Particularly preferred said amino acid is alanine, glycine, isoleucine, leucine, valine. Even more preferred said amino acid is glycine or leucine. Most preferably, it is leucine.

The "CAS RN" stated in square brackets behind the names (common names) mentioned under groups A to C corresponds to the "chemical abstract service registry number", a customary reference number which allows the substances named to be classified unambiguously, since the "CAS RN" distinguishes, inter alia, between isomers including stereoisomers.

ALS inhibitor herbicides which are preferably used for control of unwanted vegetation in *Beta vulgaris*, preferably sugar beet growing areas in which *Beta vulgaris*, preferably sugar beet plants, contain an ALS protein encoded by an endogenous ALS gene comprising an amino acid different from tryptophan at position 569 and an amino acid different from proline at position 188, and thereby providing tolerance against the ALS inhibitor herbicide(s) according to this invention belonging to group (A) are:
amidosulfuron [CAS RN 120923-37-7] (=A1-1);
chlorimuron-ethyl [CAS RN 90982-32-4] (=A1-4);
ethametsulfuron-methyl [CAS RN 97780-06-8] (=A1-8);
ethoxysulfuron [CAS RN 126801-58-9] (=A1-9);
flupyrsulfuron-methyl-sodium [CAS RN 144740-54-5] (=A1-12);
foramsulfuron [CAS RN 173159-57-4] (=A1-13);
iodosulfuron-methyl-sodium [CAS RN 144550-36-7] (=A1-16);
mesosulfuron-methyl [CAS RN 208465-21-8] (=A1-17);
metsulfuron-methyl [CAS RN 74223-64-6] (=A1-18);
monosulfuron [CAS RN 155860-63-2] (=A1-19);
nicosulfuron [CAS RN 111991-09-4] (=A1-20);
sulfosulfuron [CAS RN 141776-32-1] (=A1-28);
thifensulfuron-methyl [CAS RN 79277-27-3] (=A1-29);
tribenuron-methyl [CAS RN 101200-48-0] (=A1-31);
2-iodo-N-[(4-methoxy-6-methyl-1,3,5-triazinyl)carbamoyl]benzene-sulfonamide (=A1-39);
2-iodo-N-[(4-methoxy-6-methyl-1,3,5-triazinyl)carbamoyl]benzene-sulfonamide sodium salt (=A1-41);
(A1-83) or its sodium salt (=A1-87);
propoxycarbazone-sodium [CAS RN 181274-15-7] (=A2-2);
thiencarbazone-methyl [CAS RN 317815-83-1] (=A2-3);
florasulam [CAS RN 145701-23-1] (=A3-3);
metosulam [CAS RN 139528-85-1] (=A3-5);
pyroxsulam [CAS RN 422556-08-9] (=A3-7)
(A4-1);
(A4-2); and
(A4-3).

ALS inhibitor herbicides which are especially preferably used for control of unwanted vegetation in *Beta vulgaris* (preferably sugar beet) growing areas in which the *Beta vulgaris* (preferably sugar beet) plants contain an ALS protein encoded by an endogenous ALS gene comprising an amino acid different from tryptophan at position 569 and an amino acid different from proline at position 188, and thereby providing tolerance against the ALS inhibitor herbicide(s) according to this invention belonging to group (A) are:
amidosulfuron [CAS RN 120923-37-7] (=A1-1);
foramsulfuron [CAS RN 173159-57-4] (=A1-13);
iodosulfuron-methyl-sodium [CAS RN 144550-36-7] (=A1-16);
2-iodo-N-[(4-methoxy-6-methyl-1,3,5-triazinyl)carbamoyl]benzene-sulfonamide (=A1-39);
2-iodo-N-[(4-methoxy-6-methyl-1,3,5-triazinyl)carbamoyl]benzene-sulfonamide sodium salt A1-41;
A1-83 or its sodium salt (=A1-87);
thiencarbazone-methyl [CAS RN 317815-83-1] (=A2-3).

Another ALS inhibitor herbicide which is preferably used for control of unwanted vegetation in *Beta vulgaris* (preferably sugar beet) growing areas in which the *Beta vulgaris* (preferably sugar beet) plants contain an ALS protein encoded by an endogenous ALS gene comprising an amino acid different from tryptophan at position 569 and an amino acid different from proline at position 188, and thereby providing tolerance against the ALS inhibitor herbicide(s) according to this invention belonging to group (B) is:
imazamox [CAS RN 114311-32-9] (=B1-2).

Another ALS inhibitor herbicide which is preferably used for control of unwanted vegetation in *Beta vulgaris* (preferably sugar beet) growing areas in which the *Beta vulgaris* (preferably sugar beet) plants contain an ALS protein encoded by an endogenous ALS gene comprising an amino acid different from tryptophan at position 569 and an amino acid different from proline at position 188, and thereby providing tolerance against the ALS inhibitor herbicide(s) according to this invention belonging to group (C) is:
bispyribac-sodium [CAS RN 125401-92-5] (=C1-1).

It is to be further understood that concerning all above defined ALS inhibitor herbicides and where not already specified by the respective CAS RN, all use forms, such as acids, and salts can be applied according to the invention.

Additionally, the ALS inhibitor herbicide(s) to be used according to the invention may comprise further components, for example agrochemically active compounds of a different type of mode of action and/or the formulation auxiliaries and/or additives customary in crop protection, or may be used together with these.

In a preferred embodiment, the herbicide combinations to be used according to the invention comprise effective amounts of the ALS inhibitor herbicide(s) belonging to groups (A), (B) and/or (C) and/or have synergistic actions. The synergistic actions can be observed, for example, when applying one or more ALS inhibitor herbicide(s) belonging to groups (A), (B), and/or (C) together, for example as a coformulation or as a tank mix; however, they can also be observed when the active compounds are applied at different times (splitting). It is also possible to apply the herbicides or the herbicide combinations in a plurality of portions (sequential application), for example pre-emergence applications followed by post-emergence applications or early post-emergence applications followed by medium or late post-emergence applications. Preference is given here to the joint or almost simultaneous application of the ALS-inhibitor herbicides belonging to groups (A), (B) and/or (C) of the combination in question.

The synergistic effects permit a reduction of the application rates of the individual ALS inhibitor herbicides, a higher efficacy at the same application rate, the control of species which were as yet uncontrolled (gaps), control of species which are tolerant or resistant to individual ALS inhibitor herbicides or to a number of ALS inhibitor herbicides, an extension of the period of application and/or a reduction in the number of individual applications required and—as a result for the user—weed control systems which are more advantageous economically and ecologically.

The herbicides to be used according to this invention are all acetolactate synthase (ALS) inhibitor herbicides (which might alternatively and interchangeably also be named as "ALS inhibiting herbicides") and thus inhibit protein biosynthesis in plants.

The application rate of the ALS inhibitor herbicides belonging to groups (A), (B) or (C) (as defined above) can vary within a wide range, for example between 0.001 g and 1500 g of ai/ha (ai/ha means here and below "active substance per hectare"=based on 100% pure active compound). Applied at application rates of from 0.001 g to 1500 g of ai/ha, the herbicides belonging to classes A, B and C according to this invention, preferably the compounds A1-1; A1-4; A1-8; A1-9; A1-12; A1-13; A1-16; A1-17; A1-18; A1-19; A1-20; A1-28; A1-29; A1-31; A1-39; A1-41; A1-83; A1-87; A2-2; A2-3; A3-3; A3-5; A3-7, A4-3, control, when used by the pre- and post-emergence method, a relatively wide spectrum of harmful plants, for example of annual and perennial mono- or dicotyledonous weeds, and also of unwanted crop plants (together also defined as "unwanted vegetation).

In many applications according to the invention, the application rates are generally lower, for example in the range of from 0.001 g to 1000 g of ai/ha, preferably from 0.1 g to 500 g of ai/ha, particularly preferably from 0.5 g to 250 g of ai/ha, and even more preferably 1.0 g to 200 g of ai/ha. In cases where the application of several ALS inhibitor herbicides is conducted, the quantity represents the total quantity of all of the applied ALS inhibitor herbicides.

For example, the combinations according to the invention of ALS inhibitor herbicides (belonging to groups (A), (B) and/or (C)) allow the activity to be enhanced synergistically in a manner which, by far and in an unexpected manner, exceeds the activities which can be achieved using the individual ALS inhibitor herbicides (belonging to groups (A), (B) and/or (C)).

For combinations of ALS inhibitor herbicides, the preferred conditions are illustrated below.

Of particular interest according to present invention is the use of herbicidal compositions for control of unwanted vegetation in *Beta vulgaris* plants, preferably in sugar beet plants having a content of the following ALS inhibitor herbicides:
(A1-1)+(A1-4); (A1-1)+(A1-8); (A1-1)+(A1-9); (A1-1)+(A1-12);
(A1-1)+(A1-13); (A1-1)+(A1-16); (A1-1)+(A1-17); (A1-1)+(A1-18);
(A1-1)+(A1-19); (A1-1)+(A1-20); (A1-1)+(A1-28); (A1-1)+(A1-29);
(A1-1)+(A1-31); (A1-1)+(A1-39); (A1-1)+(A1-41); (A1-1)+(A1-83);
(A1-1)+(A1-87); (A1-1)+(A2-2); (A1-1)+(A2-3); (A1-1)+(A3-3);
(A1-1)+(A3-5); (A1-1)+(A3-7); (A1-1)+(A4-1); (A1-1)+(A4-2); (A1-1)+(A4-3);
(A1-4)+(A1-8); (A1-4)+(A1-9); (A1-4)+(A1-12); (A1-4)+(A1-13);
(A1-4)+(A1-16); (A1-4)+(A1-17); (A1-4)+(A1-18); (A1-4)+(A1-19);
(A1-4)+(A1-20); (A1-4)+(A1-28); (A1-4)+(A1-29); (A1-4)+(A1-31);
(A1-4)+(A1-39); (A1-4)+(A1-41); (A1-4)+(A1-83); (A1-4)+(A1-87);
(A1-4)+(A2-2); (A1-4)+(A2-3); (A1-4)+(A3-3); (A1-4)+(A3-5);
(A1-4)+(A3-7); (A1-4)+(A4-1); (A1-4)+(A4-2); (A1-4)+(A4-3);
(A1-8)+(A1-9); (A1-8)+(A1-12); (A1-8)+(A1-13); (A1-8)+(A1-16);
(A1-8)+(A1-17); (A1-8)+(A1-18); (A1-8)+(A1-19); (A1-8)+(A1-20);
(A1-8)+(A1-28); (A1-8)+(A1-29); (A1-8)+(A1-31); (A1-8)+(A1-39);
(A1-8)+(A1-41); (A1-8)+(A1-83); (A1-8)+(A1-87); (A1-8)+(A2-2);
(A1-8)+(A2-3); (A1-8)+(A3-3); (A1-8)+(A3-5); (A1-8)+(A3-7);
(A1-8)+(A4-1); (A1-8)+(A4-2); (A1-8)+(A4-3);
(A1-9)+(A1-12); (A1-9)+(A1-13); (A1-9)+(A1-16); (A1-9)+(A1-17);
(A1-9)+(A1-18); (A1-9)+(A1-19); (A1-9)+(A1-20); (A1-9)+(A1-28);
(A1-9)+(A1-29); (A1-9)+(A1-31); (A1-9)+(A1-39); (A1-9)+(A1-41);
(A1-9)+(A1-83); (A1-9)+(A1-87); (A1-9)+(A2-2); (A1-9)+(A2-3);
(A1-9)+(A3-3); (A1-9)+(A3-5); (A1-9)+(A3-7); (A1-9)+(A4-1);
(A1-9)+(A4-2); (A1-9)+(A4-3);
(A1-12)+(A1-13); (A1-12)+(A1-16); (A1-12)+(A1-17); (A1-12)+(A1-18);
(A1-12)+(A1-19); (A1-12)+(A1-20); (A1-12)+(A1-28); (A1-12)+(A1-29);
(A1-12)+(A1-31); (A1-12)+(A1-39); (A1-12)+(A1-41); (A1-12)+(A1-83);
(A1-12)+(A1-87); (A1-12)+(A2-2); (A1-12)+(A2-3); (A1-12)+(A3-3);
(A1-12)+(A3-5); (A1-12)+(A3-7); (A1-12)+(A4-1); (A1-12)+(A4-2); (A1-12)+(A4-3);
(A1-13)+(A1-16); (A1-13)+(A1-17); (A1-13)+(A1-18); (A1-13)+(A1-19);
(A1-13)+(A1-20); (A1-13)+(A1-28); (A1-13)+(A1-29); (A1-13)+(A1-31);
(A1-13)+(A1-39); (A1-13)+(A1-41); (A1-13)+(A1-83); (A1-13)+(A1-87);
(A1-13)+(A2-2); (A1-13)+(A2-3); (A1-13)+(A3-3); (A1-13)+(A3-5);
(A1-13)+(A3-7); (A1-13)+(A4-1); (A1-13)+(A4-2); (A1-13)+(A4-3);
(A1-16)+(A1-17); (A1-16)+(A1-18); (A1-16)+(A1-19); (A1-16)+(A1-20);
(A1-16)+(A1-28); (A1-16)+(A1-29); (A1-16)+(A1-31); (A1-16)+(A1-39);
(A1-16)+(A1-41); (A1-16)+(A1-83); (A1-16)+(A1-87); (A1-16)+(A2-2);
(A1-16)+(A2-3); (A1-16)+(A3-3); (A1-16)+(A3-5); (A1-16)+(A3-7);
(A1-16)+(A4-1); (A1-16)+(A4-2); (A1-16)+(A4-3);
(A1-17)+(A1-18); (A1-17)+(A1-19); (A1-17)+(A1-20); (A1-17)+(A1-28);
(A1-17)+(A1-29); (A1-17)+(A1-31); (A1-17)+(A1-39); (A1-17)+(A1-41);
(A1-17)+(A1-83); (A1-17)+(A1-87); (A1-17)+(A2-2); (A1-17)+(A2-3);
(A1-17)+(A3-3); (A1-17)+(A3-5); (A1-17)+(A3-7); (A1-17)+(A4-1); (A1-17)+(A4-2); (A1-17)+(A4-3);
(A1-18)+(A1-19); (A1-18)+(A1-20); (A1-18)+(A1-28); (A1-18)+(A1-29); (A1-18)+(A1-31); (A1-18)+(A1-39); (A1-18)+(A1-41); (A1-18)+(A1-83); (A1-18)+(A1-87);
(A1-18)+(A2-2); (A1-18)+(A2-3); (A1-18)+(A3-3); (A1-18)+(A3-5); (A1-18)+(A3-7); (A1-18)+(A4-1); (A1-18)+(A4-2); (A1-18)+(A4-3);
(A1-19)+(A1-20); (A1-19)+(A1-28); (A1-19)+(A1-29); (A1-19)+(A1-31); (A1-19)+(A1-39); (A1-19)+(A1-41);
(A1-19)+(A1-83); (A1-19)+(A1-87); (A1-19)+(A2-2); (A1-19)+(A2-3); (A1-19)+(A3-3); (A1-19)+(A3-5); (A1-19)+(A3-7); (A1-19)+(A4-1); (A1-19)+(A4-2); (A1-19)+(A4-3);
(A1-20)+(A1-28); (A1-20)+(A1-29); (A1-20)+(A1-31); (A1-20)+(A1-39);
(A1-20)+(A1-41); (A1-20)+(A1-83); (A1-20)+(A1-87); (A1-20)+(A2-2);

(A1-20)+(A2-3); (A1-20)+(A3-3); (A1-20)+(A3-5); (A1-20)+(A3-7);
(A1-20)+(A4-1); (A1-20)+(A4-2); (A1-20)+(A4-3);
(A1-28)+(A1-29); (A1-28)+(A1-31); (A1-28)+(A1-39); (A1-28)+(A1-41);
(A1-28)+(A1-83); (A1-28)+(A1-87); (A1-28)+(A2-2); (A1-28)+(A2-3);
(A1-28)+(A3-3); (A1-28)+(A3-5); (A1-28)+(A3-7); (A1-28)+(A4-1);
(A1-28)+(A4-2); (A1-28)+(A4-3);
(A1-29)+(A1-31); (A1-29)+(A1-39); (A1-29)+(A1-41); (A1-29)+(A1-83);
(A1-29)+(A1-87); (A1-29)+(A2-2); (A1-29)+(A2-3); (A1-29)+(A3-3);
(A1-29)+(A3-5); (A1-29)+(A3-7); (A1-29)+(A4-1); (A1-29)+(A4-2); (A1-29)+(A4-3);
(A1-31)+(A1-39); (A1-31)+(A1-41); (A1-31)+(A1-83); (A1-31)+(A1-87);
(A1-31)+(A2-2); (A1-31)+(A2-3); (A1-31)+(A3-3); (A1-31)+(A3-5);
(A1-31)+(A3-7); (A1-31)+(A4-1); (A1-31)+(A4-2); (A1-31)+(A4-3);
(A1-39)+(A1-41); (A1-39)+(A1-83); (A1-39)+(A1-87); (A1-39)+(A2-2);
(A1-39)+(A2-3); (A1-39)+(A3-3); (A1-39)+(A3-5); (A1-39)+(A3-7);
(A1-39)+(A4-1); (A1-39)+(A4-2); (A1-39)+(A4-3);
(A1-41)+(A1-83); (A1-41)+(A1-87); (A1-41)+(A2-2); (A1-41)+(A2-3);
(A1-41)+(A3-3); (A1-41)+(A3-5); (A1-41)+(A3-7); (A1-41)+(A4-1);
(A1-41)+(A4-2); (A1-41)+(A4-3);
(A1-83)+(A2-2); (A1-83)+(A2-3); (A1-83)+(A3-3); (A1-83)+(A3-5);
(A1-83)+(A3-7); (A1-83)+(A4-1); (A1-83)+(A4-2); (A1-83)+(A4-3);
(A1-87)+(A2-2); (A1-87)+(A2-3); (A1-87)+(A3-3); (A1-87)+(A3-5);
(A1-87)+(A3-7); (A1-87)+(A4-1); (A1-87)+(A4-2); (A1-87)+(A4-3);
(A2-2)+(A2-3); (A2-2)+(A3-3); (A2-2)+(A3-5); (A2-2)+(A3-7);
(A2-2)+(A4-1); (A2-2)+(A4-2); (A2-2)+(A4-3);
(A2-3)+(A3-3); (A2-3)+(A3-5); (A2-3)+(A3-7);
(A2-3)+(A4-1); (A2-3)+(A4-2); (A2-3)+(A4-3);
(A3-3)+(A3-5); (A3-3)+(A3-7);
(A3-3)+(A4-1); (A3-3)+(A4-2); (A3-3)+(A4-3);
(A3-5)+(A3-7); (A3-5)+(A4-1); (A3-5)+(A4-2); (A3-5)+(A4-3);
(A3-7)+(A4-1); (A3-7)+(A4-2); (A3-7)+(A4-3);
(A-1)+(A4-2); (A4-1)+(A4-3); and
(A4-2)+(A4-3);

Additionally, the ALS inhibitor herbicides to be used according to the invention may comprise further components, for example agrochemically active compounds of a different type of mode of action and/or the formulation auxiliaries and/or additives customary in crop protection, or may be used together with these.

The ALS inhibitor herbicide(s) to be used according to the invention or combinations of various such ALS inhibitor herbicides may furthermore comprise various agrochemically active compounds, for example from the group of the safeners, fungicides, insecticides, or from the group of the formulation auxiliaries and additives customary in crop protection.

In a further embodiment, the invention relates to the use of effective amounts of ALS inhibitor herbicide(s) (i.e. members of the groups (A), (B) and/or (C)) and non-ALS inhibitor herbicides (i.e. herbicides showing a mode of action that is different to the inhibition of the ALS enzyme [acetohydroxyacid synthase; EC 2.2.1.6] (group D herbicides) in order obtain synergistic effect for the control of unwanted vegetation. Such synergistic actions can be observed, for example, when applying one or more ALS inhibitor herbicides (i.e. members of the groups (A), (B), and/or (C)) and one or more non-ALS inhibitor herbicides (group D herbicides) together, for example as a coformulation or as a tank mix; however, they can also be observed when the active compounds are applied at different times (splitting). It is also possible to apply the ALS inhibitor herbicides and non-ALS inhibitor herbicides in a plurality of portions (sequential application), for example pre-emergence applications followed by post-emergence applications or early post-emergence applications followed by medium or late post-emergence applications. Preference is given here to the joint or almost simultaneous application of the herbicides ((A), (B) and/or (C)) and (D) of the combination in question.

Suitable partner herbicides to be applied together with ALS inhibitor herbicides are, for example, the following herbicides which differ structurally from the herbicides belonging to the groups (A), (B), and (C) as defined above, preferably herbicidally active compounds whose action is based on inhibition of, for example, acetyl coenzyme A carboxylase, PS I, PS II, HPPDO, phytoene desaturase, protoporphyrinogen oxidase, glutamine synthetase, cellulose biosynthesis, 5-enolpyruvylshikimate 3-phosphate synthetase, as described, for example, in Weed Research 26, 441-445 (1986), or "The Pesticide Manual", 14th edition, The British Crop Protection Council, 2007, or 15$^{th}$ edition 2010, or in the corresponding "e-Pesticide Manual", Version 5 (2010), in each case published by the British Crop Protection Council, (hereinbelow in short also "PM"), and in the literature cited therein. Lists of common names are also available in "The Compendium of Pesticide Common Names" on the internet. Herbicides known from the literature (in brackets behind the common name hereinafter also classified by the indicators D1 to D426), which can be combined with ALS-inhibitor herbicides of groups (A), (B) and/or (C) and to be used according to present invention are, for example, the active compounds listed below: (note: the herbicides are referred to either by the "common name" in accordance with the International Organization for Standardization (ISO) or by the chemical name, together where appropriate with a customary code number, and in each case include all use forms, such as acids, salts, esters and isomers, such as stereoisomers and optical isomers, in particular the commercial form or the commercial forms, unless the context indicates otherwise. The citation given is of one use form and in some cases of two or more use forms):

acetochlor (=D1), acibenzolar (=D2), acibenzolar-S-methyl (=D3), acifluorfen (=D4), acifluorfen-sodium (=D5), aclonifen (=D6), alachlor (=D7), allidochlor (=D8), alloxydim (=D9), alloxydim-sodium (=D10), ametryn (=D11), amicarbazone (=D12), amidochlor (=D13), aminocyclopyrachlor (=D14), aminopyralid (=D15), amitrole (=D16), ammonium sulfamate (=D17), ancymidol (=D18), anilofos (=D19), asulam (=D20), atrazine (=D21), azafenidin (=D22), aziprotryn (=D23), beflubutamid (=D24), benazolin (=D25), benazolin-ethyl (=D26), bencarbazone (=D27), benfluralin (=D28), benfuresate (=D29), bensulide (=D30), bentazone (=D31), benzfendizone (=D32), benzobicyclon (=D33), benzofenap (=D34), benzofluor (=D35), benzoylprop (=D36), bicyclopyrone (=D37), bifenox D38), bilanafos (=D39), bilanafos-sodium (=D40), bromacil (=D41), bromobutide (=D42), bromofenoxim (=D43), bromoxynil (=D44), bromuron (=D45), buminafos (=D46), busoxinone (=D47), butachlor (=D48), butafenacil (=D49), butamifos (=D50), butenachlor (=D51), butralin (=D52), butroxydim (=D53), butylate (=D54), cafenstrole (=D55), carbetamide (=D56), carfentrazone (=D57), carfentrazone-ethyl (=D58), chlomethoxyfen (=D59), chloramben (=D60), chlorazifop (=D61), chlorazifop-butyl (=D62), chlorbromuron (=D63), chlorbufam (=D64), chlorfenac (=D65), chlorfenac-sodium (=D66), chlorfenprop (=D67), chlorflurenol (=D68), chlorflurenol-methyl (=D69), chloridazon (=D70), chlormequat-chloride (=D71), chlomitrofen (=D72), chlorophthalim (=D73), chlorthal-dimethyl (=D74), chlorotoluron (=D75), cinidon (=D76), cinidon-ethyl (=D77), cinmethylin (=D78), clethodim (=D79), clodinafop (=D80), clodinafop-propargyl (=D81), clofencet (=D82), clomazone (=D83), clomeprop (=D84), cloprop (=D85), clopyralid (=D86), cloransulam (=D87), cloransulam-methyl (=D88), cumyluron (=D89), cyanamide (=D90), cyanazine (=D91), cyclanilide (=D92), cycloate (=D93), cycloxydim (=D94), cycluron (=D95), cyhalofop (=D96), cyhalofop-butyl (=D97), cyperquat (=D98), cyprazine (=D99), cyprazole (=D100), 2,4-D (=D101), 2,4-DB (=D102), daimuron/dymron (=D103), dalapon (=D104), daminozide (=D105), dazomet (=D106), n-decanol (=D107), desmedipham (=D108), desmetryn (=D109), detosyl-pyrazolate (=D110), diallate (=D111), dicamba (=D112), dichlobenil (=D113), dichlorprop (=D114), dichlorprop-P (=D115), diclofop (=D116), diclofop-methyl (=D117), diclofop-P-methyl (=D118), diethatyl (=D119), diethatyl-ethyl (=D120), difenoxuron (=D121), difenzoquat (=D122), diflufenican (=D123), diflufenzopyr (=D124), diflufenzopyr-sodium (=D125), dimefuron (=D126), dikegulac-sodium (=D127), dimefuron (=D128), dimepiperate (=D129), dimethachlor (=D130), dimethametryn (=D131), dimethenamid (=D132), dimethenamid-P (=D133), dimethipin (=D134), dimetrasulfuron (=D135), dinitramine (=D136), dinoseb (=D137), dinoterb (=D138), diphenamid (=D139), dipropetryn (=D140), diquat (=D141), diquat-dibromide (=D142), dithiopyr (=D143), diuron (=D144), DNOC (=D145), eglinazine-ethyl (=D146), endothal (=D147), EPTC (=D148), esprocarb (=D149), ethalfluralin (=D150), ethephon (=D151), ethidimuron (=D152), ethiozin (=D153), ethofumesate (=D154), ethoxyfen (=D155), ethoxyfen-ethyl (=D156), etobenzanid (=D157), F-5331 (=2-Chlor-4-fluor-5-[4-(3-fluorpropyl)-4,5-dihydro-5-oxo-1H-tetrazol-1-yl]-phenyl]-ethansulfonamid) (=D158), F-7967 (=3-[7-Chlor-5-fluor-2-(trifluormethyl)-1H-benzimidazol-4-yl]-1-methyl-6-(trifluormethyl)pyrimidin-2,4 (1H,3H)-dion) (=D159), fenoprop D160), fenoxaprop D161), fenoxaprop-P (=D162), fenoxaprop-ethyl (=D163), fenoxaprop-P-ethyl (=D164), fenoxasulfone (=D165), fentrazamide (=D166), fenuron (=D167), flamprop (=D168), flamprop-M-isopropyl (=D169), flamprop-M-methyl (=D170), fluazifop (=D171), fluazifop-P (=D172), fluazifop-butyl (=D173), fluazifop-P-butyl (=D174), fluazolate (=D175), fluchloralin (=D176), flufenacet (thiafluamide) (=D177), flufenpyr (=D178), flufenpyr-ethyl (=D179), flumetralin (=D180), flumiclorac (=D181), flumiclorac-pentyl (=D182), flumioxazin (=D183), flumipropyn (=D184), fluometuron (=D185), fluorodifen (=D186), fluoroglycofen (=D187), fluoroglycofen-ethyl (=D188), flupoxam (=D189), flupropacil (=D190), flupropanate (=D191), flurenol (=D192), flurenol-butyl (=D193), fluridone (=D194), fluorochloridone (=D195), fluroxypyr (=D196), fluroxypyr-meptyl (=D197), flurprimidol (=D198), flurtamone (=D199), fluthiacet (=D200), fluthiacet-methyl (=D201), fluthiamide (=D202), fomesafen (=203), forchlorfenuron (=D204), fosamine (=D205), furyloxyfen (=D206), gibberellic acid (=D207), glufosinate (=D208), glufosinate-ammonium (=D209), glufosinate-P (=D210), glufosinate-P-ammonium (=D211), glufosinate-P-sodium (=D212), glyphosate (=D213), glyphosate-isopropylammonium (=D214), H-9201 (=0-(2,4-Dimethyl-6-nitrophenyl)-O-ethyl-isopropylphosphoramidothioat) (=D215), halosafen (=D216), haloxyfop (=D217), haloxyfop-P (=D218), haloxyfop-ethoxyethyl (=D219), haloxyfop-P-ethoxyethyl (=D220), haloxyfop-methyl (=D221), haloxyfop-P-methyl (=D222), hexazinone (=D223), HW-02 (=1-(Dimethoxyphosphoryl)-ethyl(2,4-dichlorphenoxy)acetate) (=D224), inabenfide (=D225), indanofan (=D226), indaziflam (=D227), indol-3-acetic acid (IAA) (=D228), 4-indol-3-ylbutyric acid (IBA) (=D229), ioxynil (=D230), ipfencarbazone (=D231), isocarbamid (=D232), isopropalin (=D233), isoproturon (=D234), isouron (=D235), isoxaben (=D236), isoxachlortole (=D237), isoxaflutole (=D238), isoxapyrifop (=D239), KUH-043 (=3-({[5-(Difluormethyl)-1-methyl-3-(trifluormethyl)-1H-pyrazol-4-yl]methyl}sulfonyl)-5,5-dimethyl-4,5-dihydro-1,2-oxazol) (=D240), karbutilate (=D241), ketospiradox (=D242), lactofen (=D243), lenacil (=D244), linuron (=D245), male is hydrazide (=D246), MCPA (=D247), MCPB (=D248), MCPB-methyl, -ethyl and -sodium (=D249), mecoprop (=D250), mecoprop-sodium (=D251), mecoprop-butotyl (=D252), mecoprop-P-butotyl (=D253), mecoprop-P-dimethylammonium (=D254), mecoprop-P-2-ethylhexyl (=D255), mecoprop-P-potassium (=D256), mefenacet (=D257), mefluidide (=D258), mepiquat-chloride (=D259), mesotrione (=D260), methabenzthiazuron (=D261), metam (=D262), metamifop (=D263), metamitron (=D264), metazachlor (=D265), metazole (=D266), methiopyrsulfuron (=D267), methiozolin (=D268), methoxyphenone (=D269), methyldymron (=D270), 1-methylcyclopropen (=D271), methylisothiocyanat (=D272), metobenzuron (=D273), metobromuron (=D274), metolachlor (=D275), S-metolachlor (=D-276), metoxuron (=D277), metribuzin (=D278), molinate (=D279), monalide (=D280), monocarbamide (=D281), monocarbamide-dihydrogensulfate (=D282), monolinuron (=D283), monosulfuron-ester (=D284), monuron (=D285), MT-128 (=6-Chlor-N-[(2E)-3-chlorprop-2-en-1-yl]-5-methyl-N-phenylpyridazin-3-amine) (=D286), MT-5950 (=N-[3-Chlor-4-(1-methylethyl)-phenyl]-2-methylpentanamide) (=D287), NGGC-010 (=D288), naproanilide (=D289), napropamide (=D290), naptalam (=D291), NC-310 (=4-(2,4-Dichlorobenzoyl)-1-methyl-5-benzyloxypyrazole) (=D292), neburon (=D293), nipyraclofen (=D294), nitralin (=D295), nitrofen (=D296), nitrophenolat-sodium (isomer mixture) (=D297), nitrofluorfen (=D298), nonanoic acid (=D299), norflurazon (=D300), orbencarb (=D301), oryzalin (=D302), oxadiargyl (=D303), oxadiazon (=D304), oxaziclomefone (=D305), oxyfluorfen (=D306), paclobutrazol (=D307), paraquat (=D308), paraquat-dichloride (=D309), pelargonic acid (nonanoic acid) (=D310), pendimethalin (=D311), pendralin (=D312), pentanochlor (=D313), pentoxazone (=D314), perfluidone (=D315), pethoxamid (=D317), phenisopham (=D318), phenmedipham (=D319), phenmedipham-ethyl (=D320), picloram (=D321), picolinafen (=D322), pinoxaden (=D323), piperophos (=D324), pirifenop (=D325), pirifenop-butyl (=D326), pretilachlor (=D327), probenazole (=D328), profluazol (=D329), procyazine (=D330), prodiamine (=D331), prifluraline (=D332), profoxydim (=D333), prohexadione (=D334), prohexadione-calcium (=D335), prohydrojasmone (=D336), prometon (=D337), prometryn (=D338), propachlor (=D339), propanil (=D340), propaquizafop (=D341), propazine (=D342), propham (=D343), propisochlor (=D344), propyzamide (=D345), prosulfalin (=D346), prosulfocarb (=D347), prynachlor (=D348), pyraclonil (=D349), pyraflufen (=D350), pyraflufen-ethyl (=D351), pyrasulfotole (=D352), pyrazolynate (pyrazolate) (=D353), pyrazoxyfen (=D354), pyribambenz (=D355), pyributicarb (=D356), pyridafol (=D357), pyridate (=D358), pyriminobac (=D359), pyrimisulfan (=D360), pyroxasulfone (=D361), quinclorac (=D362), quinmerac (=D363), quinoclamine (=D364), quizalofop (=D365), quizalofop-ethyl (=D366), quizalofop-P (=D367), quizalofop-P-ethyl (=D368), quizalofop-P-tefuryl (=D369), saflufenacil (=D370), secbumeton (=D371), sethoxydim (=D372), siduron (=D373), simazine (=D374), simetryn (=D375), SN-106279 (=Methyl-(2R)-2-({7-[2-chlor-4-(trifluormethyl)phenoxy]-2-naphthyl}oxy)-propanoate) (=D376), sulcotrione (=D377), sulfallate (CDEC) (=D378), sulfentrazone (=D379), sulfosate (glyphosate-trimesium) (=D380), SYN-523 (=D381), SYP-249 (=1-Ethoxy-3-methyl-1-oxobut-3-en-2-yl-5-[2-chlor-4-(trifluormethyl)phenoxy]-2-nitrobenzoate) (=D382), tebutam (=D383), tebuthiuron (=D384), tecnazene (=D385), tefuryltrione (=D386), tembotrione (=D387), tepraloxydim (=D388), terbacil (=D389), terbucarb (=D390), terbuchlor (=D391), terbumeton (=D392), terbuthylazine (=D393), terbutryn (=D394), thenylchlor (=D395), thiafluamide (=D396), thiazafluron (=D397), thiazopyr (=D398), thidiazimin (=D399), thidiazuron (=D400), thiobencarb (=D401), tiocarbazil (=D402), topramezone (=D403), tralkoxydim (=D404), triallate (=D405), triaziflam (=D406), triazofenamide (=D407), trichloracetic acid (TCA) (=D408), triclopyr (=D409), tridiphane (=D410), trietazine (=D411), trifluralin (=D412), trimeturon (=D413), trinexapac (=D414), trinexapac-ethyl (=D415), tsitodef (=D416), uniconazole (=D417), uniconazole-P (=D418), vernolate (=D419), ZJ-0862 (=3,4-Dichlor-N-{2-[(4,6-dimethoxypyrimidin-2-yl)oxy]benzyl}aniline) (=D420), and the below compounds defined by their chemical structure, respectively:

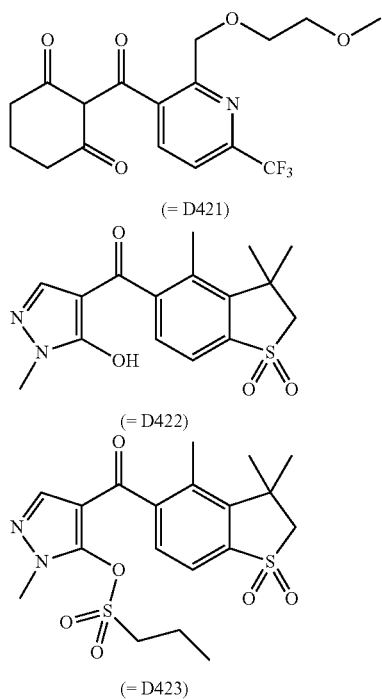

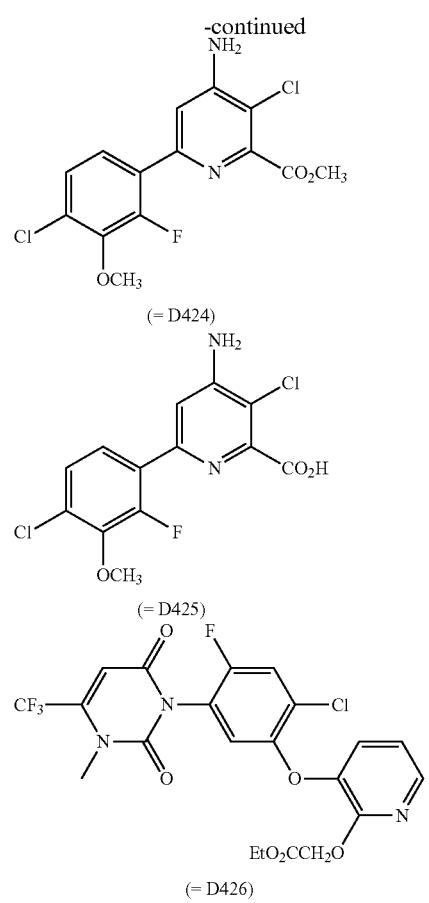

Preferred herbicides which differ structurally and via their mode of action from the ALS inhibitor herbicides belonging to the groups (A), (B), and (C) as defined above and to be applied according to the persent invention for control of unwanted vegetation in ALS inhibitor herbicide tolerant Beta vulgaris plants, preferably sugar beet plants comprising mutations in the ALS gene thereby encoding an ALS polypeptide having an amino acid that is different from the naturally occurring tryptophan at position 569 and having an amino acid that is different from the naturally occurring proline at position 188, preferably the tryptophan of the wild-type ALS protein is substituted by a leucine at position 569 and/or the proline of the wild-type ALS protein is substituted by a serine at position 188, are those belonging to the group of:

chloridazon (=D70), clethodim (=D79), clodinafop (=D80), clodinafop-propargyl (=D81), clopyralid (=D86), cycloxydim (=D94), desmedipham (=D108), dimethenamid (=D132), dimethenamid-P (=D133), ethofumesate (=D154), fenoxaprop (=D161), fenoxaprop-P (=D162), fenoxaprop-ethyl (=D163), fenoxaprop-P-ethyl (=D164), fluazifop (=D171), fluazifop-P (=D172), fluazifop-butyl (=D173), fluazifop-P-butyl (=D174), glufosinate (=D208), glufosinate-ammonium (=D209), glufosinate-P (=D210), glufosinate-P-ammonium (=D211), glufosinate-P-sodium (=D212), glyphosate (=D213), glyphosate-isopropylammonium (=D214), haloxyfop (=D217), haloxyfop-P (=D218), haloxyfop-ethoxyethyl (=D219), haloxyfop-P-ethoxyethyl (=D220), haloxyfop-methyl (=D221), haloxyfop-P-methyl (=D222), lenacil (=D244), metamitron (=D264), phenmedipham (=D319), phenmedipham-ethyl (=D320), propaquizafop (=D341), quinmerac (=D363), quizalofop (=D365), quizalofop-ethyl (=D366), quizalofop-P (=D367), quizalofop-P-ethyl (=D368), quizalofop-P-tefuryl (=D369), sethoxydim (=D372).

Even more preferred further herbicides which differ from the ALS inhibitor herbicides belonging to the groups (A), (B), and (C) as defined above and to be applied according to the invention in connection with ALS inhibitor herbicides belonging to the groups (A), (B), and (C) are those belonging to the group of:

desmedipham (=D108), ethofumesate (=D154), glufosinate (=D208), glufosinate-ammonium (=D209), glufosinate-P (=D210), glufosinate-P-ammonium (=D211), glufosinate-P-sodium (=D212), glyphosate (=D213), glyphosate-isopropylammonium (=D214), lenacil (=D244), metamitron (=D264), phenmedipham (=D319), phenmedipham-ethyl (=D320).

Mixtures containing ALS inhibitor herbicides and non-ALS inhibitor herbicides, compositions comprising mixtures of one or more ALS inhibitor herbicide(s) (compounds belonging to one or more of groups (A), (B) and (C)) and non-ALS inhibitor herbicide(s) (group (D) members; as defined above) that are of very particular interest in order to be used according to present invention for control of unwanted vegetation are:
(A1-1)+(D108); (A1-1)+(D154); (A1-1)+(D208); (A1-1)+(D209);
(A1-1)+(D210); (A1-1)+(D212); (A1-1)+(D213); (A1-1)+(D214);
(A1-1)+(D244); (A1-1)+(D264); (A1-1)+(D319); (A1-1)+(D320).
(A1-13)+(D108); (A1-13)+(D154); (A1-13)+(D208); (A1-13)+(D209);
(A1-13)+(D210); (A1-13)+(D212); (A1-13)+(D213); (A1-13)+(D214);
(A1-13)+(D244); (A1-13)+(D264); (A1-13)+(D319); (A1-13)+(D320).
(A1-16)+(D108); (A1-16)+(D154); (A1-16)+(D208); (A1-16)+(D209);
(A1-16)+(D210); (A1-16)+(D212); (A1-16)+(D213); (A1-16)+(D214);
(A1-16)+(D244); (A1-16)+(D264); (A1-16)+(D319); (A1-16)+(D320).
(A1-39)+(D108); (A1-39)+(D154); (A1-39)+(D208); (A1-39)+(D209);
(A1-39)+(D210); (A1-39)+(D212); (A1-39)+(D213); (A1-39)+(D214);
(A1-39)+(D244); (A1-39)+(D264); (A1-39)+(D319); (A1-39)+(D320).
(A1-41)+(D108); (A1-41)+(D154); (A1-41)+(D208); (A1-41)+(D209);
(A1-41)+(D210); (A1-41)+(D212); (A1-41)+(D213); (A1-41)+(D214);
(A1-41)+(D244); (A1-41)+(D264); (A1-41)+(D319); (A1-41)+(D320).
(A1-83)+(D108); (A1-83)+(D154); (A1-83)+(D208); (A1-83)+(D209);
(A1-83)+(D210); (A1-83)+(D212); (A1-83)+(D213); (A1-83)+(D214);
(A1-83)+(D244); (A1-83)+(D264); (A1-83)+(D319); (A1-83)+(D320).
(A1-87)+(D108); (A1-87)+(D154); (A1-87)+(D208); (A1-87)+(D209);
(A1-87)+(D210); (A1-87)+(D212); (A1-87)+(D213); (A1-87)+(D214);
(A1-87)+(D244); (A1-87)+(D264); (A1-87)+(D319); (A1-87)+(D320).
(A2-3)+(D108); (A2-3)+(D154); (A2-3)+(D208); (A2-3)+(D209);
(A2-3)+(D210); (A2-3)+(D212); (A2-3)+(D213); (A2-3)+(D214);
(A2-3)+(D244); (A2-3)+(D264); (A2-3)+(D319); (A2-3)+(D320).
(B1-2)+(D108); (B1-2)+(D154); (B1-2)+(D208); (B1-2)+(D209);
(B1-2)+(D210); (B1-2)+(D212); (B1-2)+(D213); (B1-2)+(D214);
(B1-2)+(D244); (B1-2)+(D264); (B1-2)+(D319); (B1-2)+(D320).
(C1-1)+(D108); (C1-1)+(D154); (C1-1)+(D208); (C1-1)+(D209);
(C1-1)+(D210); (C1-1)+(D212); (C1-1)+(D213); (C1-1)+(D214);
(C1-1)+(D244); (C1-1)+(D264); (C1-1)+(D319); (C1-1)+(D320).

The application of ALS inhibitor herbicides also act efficiently on perennial weeds which produce shoots from rhizomes, root stocks and other perennial organs and which are difficult to control. Here, the substances can be applied, for example, by the pre-sowing method, the pre-emergence method or the post-emergence method, for example jointly or separately. Preference is given, for example, to application by the post-emergence method, in particular to the emerged harmful plants.

Specific examples may be mentioned of some representatives of the monocotyledonous and dicotyledonous weed flora which can be controlled by the ALS inhibitor herbicides, without the enumeration being restricted to certain species.

Examples of weed species on which the application according to present invention act efficiently are, from amongst the monocotyledonous weed species, *Avena* spp., *Alopecurus* spp., *Apera* spp., *Brachiaria* spp., *Bromus* spp., *Digitaria* spp., *Lolium* spp., *Echinochloa* spp., *Panicum* spp., *Phalaris* spp., Poa spp., *Setaria* spp. and also *Cyperus* species from the annual group, and, among the perennial species, *Agropyron, Cynodon, Imperata* and Sorghum and also perennial *Cyperus* species.

In the case of the dicotyledonous weed species, the spectrum of action extends to genera such as, for example, *Abutilon* spp., *Amaranthus* spp., *Chenopodium* spp., *Chrysanthemum* spp., Galium spp., *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., among the annuals, and *Convolvulus, Cirsium, Rumex* and *Artemisia* in the case of the perennial weeds.

It is preferred that the *Beta vulgaris* plant, preferably sugar beet plant, to which one or more ALS inhibitor herbicide(s) alone or in combination with one or more herbicide(s) that do(es) not belong to the class of ALS inhibitor herbicides are applied for control of unwanted vegetation in *Beta vulgaris*, preferably in sugar beet growing areas in which *Beta vulgaris* plants, preferably sugar beet comprise mutations in the ALS gene thereby encoding an ALS polypeptide having an amino acid that is different from the naturally occurring tryptophan at position 569 and having an amino acid that is different from the naturally occurring proline at position 188, is orthoploid or anorthoploid. Herein, an orthoploid plant may preferably be haploid, diploid, tetraploid, hexaploid, octaploid, decaploid or dodecaploid, while an anorthoploid plant may preferably be triploid or pentaploid.

As used herein unless clearly indicated otherwise, the term "plant" intended to mean a plant at any developmental stage.

It might be, that—depending on the respective genetic background—*Beta vulgaris* plants of the same genetic background in which such mutation is only heterozygously present, the herbicide tolerant *Beta vulgaris* plants which are homozygous for the non-transgenic mutation of the endegenous ALS gene reveal a better agronomical level of ALS inhibitor herbicide tolerance.

In this context "homozygous" indicates that a plant of the present invention has two copies of the same allele on different DNA strands, in particular at the ALS gene locus.

Accordingly, when used herein the term "heterozygous" or "heterozygously" means that a plant of the present invention has different alleles at a particular locus, in particular at the ALS gene locus.

Therefore, the present invention relates to the use of one or more ALS inhibitor herbicide(s) alone or in combination with one or more non-ALS inhibitor herbicide(s) for weed control in *Beta vulgaris*, preferably in sugar beet, growing areas in which the *Beta vulgaris* plants, preferably sugar beet plants, comprise mutations in the codon of an endogenous ALS gene encoding an ALS protein containing (i) an amino acid that is different from tryptophan at position 569, preferably the tryptophan of the wild-type ALS protein is substituted by a leucine at position 569, and (ii) an amino acid that is different from proline at position 188, preferably the proline of the wild-type ALS protein is substituted by a serine at position 188. These mutations of the endogeneous ALS gene can be heterozygously present, and can preferably be the only two mutations of the ALS gene. More preferably, the respective mutations can be homozygously present, and most preferably, the respective mutation is homozygously present as the only two mutations of the endogenous ALS gene.

Owing to their herbicidal and plant growth-regulatory properties, ALS inhibitor herbicides belonging to one or more of the groups (A), (B), and (C) either alone or in combination with non-ALS inhibitor herbicides can be employed for controlling harmful plants in known *Beta vulgaris*, preferably sugar beet plants but also in tolerant or genetically modified crop plants that do already exists or need still to be developed. In general, the transgenic plants are distinguished by specific advantageous properties, in addition to tolerances to the ALS inhibitor herbicides according to the invention, for example, by tolerances to non-ALS inhibitor herbicides, resistances to plant diseases or the causative organisms of plant diseases such as certain insects or microorganisms, such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which exhibit tolerance to non-ALS inhibitor herbicides, transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology are known in principle with the aid of which novel transgenic plants with modified properties can be generated; see, for example, Sambrook et al., 1989, Molecular Cloning, A Laboratory Manual, $2^{nd}$ Edition, Cold Spring Harbor Laboratory Press, Cold Spring Harbor, N.Y.; or Winnacker "Gene and Klone", VCH Weinheim $2^{nd}$ Edition 1996 or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, the abovementioned standard methods allow base exchanges to be carried out, subsequences to be removed, or natural or synthetic sequences to be added. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give rise to entire plants. Thus, transgenic *Beta vulgaris* plants, preferably sugar beet plants can be obtained whose properties are altered by overexpression, suppression or inhibition of homologous (=natural) genes or gene sequences or the expression of heterologous (=foreign) genes or gene sequences.

The present invention furthermore provides a method for controlling unwanted vegetation in *Beta vulgaris* plants, preferably in sugar beet, which comprises applying one or more ALS inhibitor herbicides belonging to groups (A), (B) and/or (C) to the plants (for example harmful plants, such as monocotyledonous or dicotyledonous weeds or unwanted crop plants), the seed (seeds or vegetative propagation organs, such as tubers or shoot parts) or to the area in which the plants grow (for example the area under cultivation), for example together or separately.

The present invention furthermore provides a method for controlling unwanted vegetation in *Beta vulgaris* plants, preferably in sugar beet, which comprises applying one or more ALS inhibitor herbicide(s) belonging to groups (A), (B) and/or (C) alone or in combination with non-ALS inhibitor herbicides belonging to class (D) compound according to the invention to the plants (for example harmful plants, such as monocotyledonous or dicotyledonous weeds or unwanted crop plants), the seed (seeds or vegetative propagation organs, such as tubers or shoot parts) or to the area in which the plants grow (for example the area under cultivation), for example together or separately. One or more non-ALS inhibitor herbicides may be applied in combination with one or more ALS inhibitor herbicide(s) before, after or simultaneously with the ALS inhibitor herbicide(s) to the plants, the seed or the area in which the plants grow (for example the area under cultivation).

"Unwanted plants" or "unwanted vegetation" are to be understood as meaning all plants which grow in locations where they are unwanted. This can, for example, be harmful plants (for example monocotyledonous or dicotyledonous weeds or unwanted crop plants).

Attached Sequences (SEQ.ID.NOs: 1 to 8)

SEQ.ID.NOs: 1 and 7 represent wild-type nucleic acid sequences of sugar beet.

SEQ.ID.NOs: 2 and 8 represent the ALS protein sequences encoded by the SEQ.ID.NOs: 1 and 7, respectively.

SEQ.ID.NO:3 represents the nucleic acid sequence of a mutated ALS gene encoding sugar beet ALS protein comprising a Trp Leu mutation.

SEQ.ID.NO:4 represents the Trp→Leu mutated ALS protein at position 569 which is encoded by nucleic acid sequence SEQ.ID.NO:3.

SEQ.ID.NO:5 represents the nucleic acid sequence of a mutated ALS gene encoding sugar beet ALS protein comprising a Pro→Ser mutation.

SEQ.ID.NO:6 represents the Pro→Ser mutated ALS protein at position 188 which is encoded by nucleic acid sequence SEQ.ID.NO:5.

Preferably, (one allele of) the ALS gene of a *Beta vulgaris* plant, preferably a sugar beet plant used in the context of the present invention corresponds to SEQ.ID.NO:3 or SEQ.ID.NO:5.

Preferably, a *Beta vulgaris* plant, preferably a sugar beet plant used in the context of the present comprises SEQ.ID.NO:3 (in one allele) and/or SEQ.ID.NO:5 (in the second allele), more preferably, a *Beta vulgaris* plant, preferably a sugar beet plant used in the context of the present comprises SEQ.ID.NO:3 in one allele and SEQ.ID.NO:5 in the second allele.

Alternatively, a *Beta vulgaris* plant, preferably a sugar beet plant used in the context of the present invention comprises SEQ.ID.NO:3 (or SEQ.ID.NO:4) and/or SEQ.ID.NO:5 (or SEQ.ID.NO:6).

Alternatively, a *Beta vulgaris* plant, preferably a sugar beet plant used in the context of the present invention comprises SEQ.ID.NO:3 (in one allele) and either SEQ.ID.NO:1, or SEQ.ID.NO:7 (in the second allele).

Such mutated sugar beet plants are resistant to one or several ALS inhibitor(s) used, such as a sulfonylurea (e.g. foramsulfuron) and advantageously additionally to other ALS inhibitor(s), preferably selected from the group consisting of iodosulfuron, amidosulfuron and thiencarbazone-methyl.

In a preferred embodiment according to the present invention relates to a use according to the present invention (as defined hereinbefore) and a corresponding method (as defined hereinbefore), wherein the *Beta vulgaris* plants correspond to the deposit under NCIMB 42050.

The herbicide combinations to be used according to the invention can be prepared by known processes, for example as mixed formulations of the individual components, if appropriate with further active compounds, additives and/or customary formulation auxiliaries, which combinations are then applied in a customary manner diluted with water, or as tank mixes by joint dilution of the components, formulated separately or formulated partially separately, with water. Also possible is the split application of the separately formulated or partially separately formulated individual components.

It is also possible to apply ALS inhibitor herbicides or the combination comprising ALS inhibitor herbicide(s) and non-ALS inhibitor herbicide(s) in a plurality of portions (sequential application) using, for example, pre-emergence applications followed by post-emergence applications or using early post-emergence applications followed by medium or late post-emergence applications. Preference is given here to the joint or almost simultaneous application of the active compounds of the combination in question.

The herbicides belonging to any of the above defined groups (A), (B), (C) and (D) and to be applied according to present invention can be converted jointly or separately into customary formulations, such as solutions, emulsions suspensions, powders, foams, pastes, granules, aerosols, natural and synthetic materials impregnated with active compound and microencapsulations in polymeric materials. The formulations may comprise the customary auxiliaries and additives.

These formulations are produced in a known manner, for example by mixing the active compounds with extenders, that is liquid solvents, pressurized liquefied gases and/or solid carriers, if appropriate with the use of surfactants, that is emulsifiers and/or dispersants, and/or foam formers.

If the extender used is water, it is also possible to use, for example, organic solvents as auxiliary solvents. Suitable liquid solvents are essentially: aromatics, such as xylene, toluene, alkylnaphthalenes, chlorinated aromatics or chlorinated aliphatic hydrocarbons, such as chlorobenzenes, chloroethylenes, or methylene chloride, aliphatic hydrocarbons, such as cyclohexane or paraffins, for example mineral oil fractions, mineral and vegetable oils, alcohols, such as butanol or glycol, and ethers and esters thereof, ketones, such as acetone, methyl ethyl ketone, methyl isobutyl ketone or cyclohexanone, strongly polar solvents, such as dimethylformamide or dimethyl sulfoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite and dolomite, and also synthetic granules of inorganic and organic meals, and granules of organic material, such as sawdust, coconut shells, corn cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins and synthetic phospholipids, can be used in the formulations. Other possible additives are mineral and vegetable oils.

The herbicidal action of the herbicide combinations to be used according to the invention can be improved, for example, by surfactants, preferably by wetting agents from the group of the fatty alcohol polyglycol ethers. The fatty alcohol polyglycol ethers preferably comprise 10-18 carbon atoms in the fatty alcohol radical and 2-20 ethylene oxide units in the polyglycol ether moiety. The fatty alcohol polyglycol ethers may be present in nonionic form, or ionic form, for example in the form of fatty alcohol polyglycol ether sulfates, which may be used, for example, as alkali metal salts (for example sodium salts and potassium salts) or ammonium salts, or even as alkaline earth metal salts, such as magnesium salts, such as $C_{12}/C_{14}$-fatty alcohol diglycol ether sulfate sodium (Genapol® LRO, Clariant GmbH); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, $(C_{10}-C_{18})$-, preferably $(C_{10}-C_{14})$-fatty alcohol polyglycol ethers (for example isotridecyl alcohol polyglycol ethers) which comprise, for example, 2-20, preferably 3-15, ethylene oxide units, for example those from the Genapol® X-series, such as Genapol® X-030, Genapol® X-060, Genapol® X-080 or Genapol® X-150 (all from Clariant GmbH).

The present invention further comprises the combination of ALS inhibitor herbicides belonging to any of the groups (A), (B), and (C) according to present invention with the wetting agents mentioned above from the group of the fatty alcohol polyglycol ethers which preferably contain 10-18 carbon atoms in the fatty alcohol radical and 2-20 ethylene oxide units in the polyglycol ether moiety and which may be present in nonionic or ionic form (for example as fatty alcohol polyglycol ether sulfates). Preference is given to $C_{12}/C_{14}$-fatty alcohol diglycol ether sulfate sodium (Genapol® LRO, Clariant GmbH) and isotridecyl alcohol polyglycol ether having 3-15 ethylene oxide units, for example from the Genapol® X-series, such as Genapol® X-030, Genapol® X-060, Genapol® X-080 and Genapol® X-150 (all from Clariant GmbH). Furthermore, it is known that fatty alcohol polyglycol ethers, such as nonionic or ionic fatty alcohol polyglycol ethers (for example fatty alcohol polyglycol ether sulfates) are also suitable for use as penetrants and activity enhancers for a number of other herbicides (see, for example, EP-A-0502014).

Furthermore, it is known that fatty alcohol polyglycol ethers, such as nonionic or ionic fatty alcohol polyglycol ethers (for example fatty alcohol polyglycol ether sulfates) are also suitable for use as penetrants and activity enhancers for a number of other herbicides (see, for example, EP-A-0502014).

The herbicidal action of the herbicide combinations according to the invention can also be enhanced by using vegetable oils. The term vegetable oils is to be understood as meaning oils of oleaginous plant species, such as soybean oil, rapeseed oil, corn oil, sunflower oil, cottonseed oil, linseed oil, coconut oil, palm oil, thistle oil or castor oil, in particular rapeseed oil, and also their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-, fatty acids. The $C_{10}$-$C_{22}$-fatty acid esters are, for example, esters of unsaturated or saturated $C_{10}$-$C_{22}$-fatty acids, in particular those having an even number of carbon atoms, for example erucic acid, lauric acid, palmitic acid and in particular $C_{18}$-fatty acids, such as stearic acid, oleic acid, linoleic acid or linolenic acid.

Examples of $C_{10}$-$C_{22}$-fatty acid esters are esters obtained by reacting glycerol or glycol with the $C_{10}$-$C_{22}$-fatty acids contained, for example, in oils of oleaginous plant species, or $C_1$-$C_{20}$-alkyl-$C_{10}$-$C_{22}$-fatty acid esters which can be obtained, for example, by transesterification of the aforementioned glycerol- or glycol-$C_{10}$-$C_{22}$-fatty acid esters with $C_{10}$-$C_{22}$-alcohols (for example methanol, ethanol, propanol or butanol). The transesterification can be carried out by known methods as described, for example, in Römpp Chemie Lexikon, 9th edition, Volume 2, page 1343, Thieme Verlag Stuttgart.

Preferred $C_1$-$C_{20}$-alkyl-$C_{10}$-$C_{22}$-fatty acid esters are methyl esters, ethyl esters, propyl esters, butyl esters, 2-ethylhexyl esters and dodecyl esters. Preferred glycol- and glycerol-$C_{10}$-$C_{22}$-fatty acid esters are the uniform or mixed glycol esters and glycerol esters of $C_{10}$-$C_{22}$-fatty acids, in particular fatty acids having an even number of carbon atoms, for example erucic acid, lauric acid, palmitic acid and, in particular, $C_{18}$-fatty acids, such as stearic acid, oleic acid, linoleic acid or linolenic acid.

In the herbicidal compositions to be used according to the invention, the vegetable oils can be present, for example, in the form of commercially available oil-containing formulation additives, in particular those based on rapeseed oil, such as Hasten® (Victorian Chemical Company, Australia, hereinbelow referred to as Hasten, main ingredient: rapeseed oil ethyl ester), Actirob®B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

In a further embodiment, herbicidal combinations to be used according to present invention can be formulated with the vegetable oils mentioned above, such as rapeseed oil, preferably in the form of commercially available oil-containing formulation additives, in particular those based on rapeseed oil, such as Hasten® (Victorian Chemical Company, Australia, hereinbelow referred to as Hasten, main ingredient: rapeseed oil ethyl ester), Actirob®B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

It is possible to use colorants, such as inorganic pigments, for example iron oxide, titanium oxide, Prussian Blue, and organic dyes, such as alizarin dyes, azo dyes and metal phthalocyanine dyes, and trace nutrients such as salts of iron, manganese, boron, copper, cobalt, molybdenum and zinc.

The formulations to be used according to present invention generally comprise from 0.1 to 95% by weight of active compounds, preferably from 0.5 to 90% by weight.

As such or in their formulations, the ALS inhibitor herbicides belonging to any of the above defined groups (A), (B), and (C) can also be used as a mixture with other agrochemically active compounds, such as known non-ALS inhibitor herbicides, for controlling unwanted vegetation, for example for controlling weeds or for controlling unwanted crop plants, finished formulations or tank mixes, for example, being possible.

The use of a mixture of ALS inhibitor herbicides belonging to any of the above defined groups (A), (B), and (C) with other known active compounds, such as fungicides, insecticides, acaricides, nematicides, safeners, bird repellants, plant nutrients and soil structure improvers is likewise possible.

The ALS inhibitor herbicides belonging to any of the above defined groups (A), (B), (C) can be used as such, in the form of their formulations or in the use forms prepared therefrom by further dilution, such as ready-to-use solutions, suspensions, emulsions, powders, pastes and granules. Application is carried out in a customary manner, for example by watering, spraying, atomizing, broadcasting.

According to the invention, one or more of the ALS inhibitor herbicides belonging to any of the above defined groups (A), (B), and (C) can be applied either alone or in combination with one or more non-ALS inhibitor herbicides belonging to group (D) to the plants (for example harmful plants, such as monocotyledonous or dicotyledonous weeds or unwanted crop plants), the seed (for example grains, seeds or vegetative propagation organs, such as tubers or shoot parts with buds) or the area under cultivation (for example the soil), preferably to the green plants and parts of plants and, if appropriate, additionally the soil. One possible use is the joint application of the active compounds in the form of tank mixes, where the optimally formulated concentrated formulations of the individual active compounds are, together, mixed in a tank with water, and the spray liquor obtained is applied.

BIOLOGICAL EXAMPLES

Selection for obtaining ALS inhibitor tolerant *Beta vulgaris* plants for use in the context of the present invention The making, selection and propagation of the respective ALS inhibitor herbicide tolerant *Beta vulgaris* mutants and their progenies that were used in all the biological examples disclosed subsequently is described in detail in the European Patent Application 12196858.0 (Bayer CropScience AG being co-applicant) having the title "Method to develop herbicide-resistant sugar beet plants" which was filed on 13 Dec. 2012 at the European Patent Office. Therefore, these respective techniques concerning the preparation of such ALS inhibitor herbicide tolerant *Beta vulgaris* mutants, especially sugar beet mutants comprising mutations in the endogenous ALS gene encoding an ALS polypeptide containing an amino acid that is different from tryptophan at position 569 and an amino acid that is different from proline at position 188 are described herein only in brief and the content of the above cited European Patent Application 12196858.0 is referenced in its entirety.

A suitable method for producing a sugar beet mutant being resistant to one or more inhibitor(s) of the acetohydroxyacid synthase enzyme (ALS) for use in the context of the present invention preferably comprises the steps of:

obtaining protoplasts from stomatal guard cells isolated from a sugar beet plant;

applying to an in vitro culture of the said protoplasts a composition comprising one or more ALS inhibitor(s) at a concentration that is lethal to more than 99.9% of the in vitro cultured cells (yet allowing some mutants to escape); and regenerating sugar beet plants from the surviving cells of the said in vitro cultured cells, wherein the said stomatal guard cells protoplasts are pre selected for their capacity to regenerate into a sugar beet plant and/or wherein the said ALS inhibitor(s) is/are applied to more than 2 000 000 of the said protoplasts, said method preferably comprising the sub-steps of isolating stomatal guard cells protoplasts from sugar beet plants of different genotypes and measuring for each genotype the proportion of the said protoplasts that is growing when the said protoplasts are put in culture.

It can be stated that this method is very useful to develop plants having evolved mutations causing a resistance to an herbicide, especially since this method does not involve the use of foreign DNA and/or the introduction of DNA vectors encoding genetic elements already known to confer resistance to ALS inhibitors.

Example 1 Selection of Sugar Beet Genotypes (Lines) for Well-Regenerating Protoplasts Because mutated sugar beet were successfully generated in the art (e.g. WO 98/02527) upon the addition of ALS herbicide to calli being explants from wild-type sugar beet, firstly the sugar beet genotype (line) derived from the line of WO 98/02527 was selected and protoplasts from their stomatal guard cells isolated therefrom. Several millions of these protoplasts were isolated as described in WO 95/10178, placed in culture medium comprising alginate, and treated with MS culture medium comprising $10^{-9}$ to $10^{-6}$ mol/l foramsulfuron.

By using the approach as described in WO 98/02527 and WO 95/10178 several sugar beet plant genotypes were compared for their capacity of regeneration from stomatal guard cells protoplasts. As a result, a genotype was selected having more than 0.25% of stomatal guard cells protoplasts that are able to grow in vitro.

Example 2 Herbicide Treatment of Protoplasts

Subsequently, the same approach as described in WO 98/02527 and WO 95/10178 was applied, but relying on well growing stomatal guard cells protoplasts (as identified in Example 1; other sugar beet plants having a high proportion of growing stomatal guard cell protoplasts).

By treating about 68 millions of well-growing stomatal guard cell protoplasts with an ALS herbicide composition comprising up to $10^{-6}$M foramsulfuron, a total of 46 calli were obtained.

One regenerated plant showed a mutation in the ALS gene: a mutation in the codon for tryptophan at position 569 (corresponding to tryptophan at position 574 in *Arabidopsis thaliana*). The two alleles of the ALS genes of this mutant are encoded by SEQ.ID.NO:3 and SEQ.ID.NO:7. Other grown calli were sequenced and have mutations in the ALS gene, (including mutations at other positions) but did not regenerate into a plant.

Obtained seeds, containing the tryptophan to leucin mutation at position 569 and the proline to serine mutation at position 188 of the ALS protein encoded by the endogenous sugar beet ALS gene have been deposited with the NCIMB, Aberdeen, UK, under Number NCIMB 42050 (Bayer CropScience AG being co-depositor).

Example 3 ALS Inhibitor Treatment of Sugar Beets

The behaviour of regenerated sugar beet plants having the mutated SEQ.ID.NO:3 (heterozygote for this mutation) and a wild-type sugar beet commercial variety was compared.

The (heterozygote) mutated variety showed good resistance to foramsulfuron (12.5 g/ha; up to 3 applications), even when the herbicide has been combined with an organic compound (25 g/ha rapeseed oil methyl ester) to boost its effect.

As expected, the wild-type plant was very sensitive to foramsulfuron, even after the first application.

The same experiment was performed using amidosulfuron (15 g/ha), and yielded the same level of resistance in the mutated plants.

On the other hand, the wild-type plants were very sensitive to amidosulfuron, especially when combined with the organic compound, and/or after several applications of amidosulfuron.

The same experiment was performed using iodosulfuron (3.5 g/ha), and demonstrated a good level of resistance in the mutated plants when iodosulfuron was added, but this resistance declined when iodosulfuron is applied together with the organic compound.

As expected, the wild-type plant was very sensitive to iodosulfuron even after one application and without the organic compound.

The same experiment was performed using 7.5 g/ha thiencarbazone-methyl, and yielded about the same level of resistance as for iodosulfuron in the mutated plants.

The wild-type plant was very sensitive to thiencarbazone-methyl at all the tested concentrations and regardless of the addition of the organic compound.

It can be concluded that, by comparison to the wild-type, the mutated sugar beet plant comprising SEQ.ID.NO:3 (deposited under the Budapest Treaty NCIMB 42051) offers the best resistance against foramsulfuron.

It can further be concluded that this (heterozygote) mutated plant has further acquired some (although partial) resistance towards other ALS inhibitors, including towards inhibitors belonging to other chemical classes.

Example 4 ALS Inhibitor Treatment of Sugar Beets Having Further Mutations in the ALS Gene Subsequently, a mutated sugar beet plant was developed comprising SEQ.ID.NO:3 and SEQ.ID.NO:5 (on two different alleles). Such resulting dual mutant has been deposited under the Budapest Treaty under NCIMB 42050. A plant comprising both SEQ.ID.NO:3 and SEQ.ID.NO:5 can be generated by relying on several techniques, including, for instance, a subsequent mutagenesis step applied to the single mutant NCIMB 42051.

Then the resistance of this dual mutant plant (a mutation in one allele at amino acid 569 and a mutation in the other allele at amino acid 188) was compared with the single mutant (a mutation at position 569) sugar beet.

The dual mutant plant line at least keeps all the resistance features as in Example 3, and has also acquired a good resistance (compatible with field application) towards thiencarbazone-methyl and towards amidosulfuron treatments, even when put in composition with organic compounds.

Therefore, this dual mutant plant displays improved, synergistic, resistance towards several ALS inhibitors by comparison to the resistance attributed to the single mutant plant (at position 569 in the ALS gene).

Example 5 Greenhouse Trials: ALS Inhibitor Treatment of Different Sugar Beets in Direct Comparison Mutated sugar beet plants comprising SEQ.ID.NO:3 and SEQ.ID.NO:5 (on two different alleles) for use in the context of the present invention (as described in Example 4 above, "Line A") were treated with different ALS inhibitors in direct comparison with sugar beet plants where the tryptophan at position 569 of the encoded ALS enzyme is substituted by a leucine ("Line B"), with sugar beet plants described in WO 98/02527 where the proline at position 188 of the encoded ALS enzyme is substituted by a serine ("Line C"), and a traditional variety (wild-type) sugar beet plant not having a mutation at positions 569 and 188 ("Line WT").

Several groups of seeds of the four different mentioned sugar beet plants were sown separately in the greenhouse and grew up to stage BBCH 14 for *Beta vulgaris* L. ssp. *vulgaris* (i.e. 4 leaves (the second pair) unfolded) according to the BBCH monograph "Growth stages of mono- and dicotyledonous plants", 2nd edition, 2001, ed. Uwe Meier, Federal Biological Research Centre for Agriculture and Forestry (Biologische Bundesanstalt für Land and Forstwirtschaft). Subsequently, the resulting separate groups of sugar beet plants were each individually treated with an ALS inhibitor (ALS-in) in the amounts (g/ha) indicated in Table 1.

On day 14 after application of the respective ALS inhibitor, the damage (i.e. the phytotoxicity) for each group of sugar beet plants was rated on a stratified scale from 0% (i.e. no damage, no phytotoxicity) to 100% (i.e. the plants were completely killed). The average rating for each group of plants is also shown in Table 1.

TABLE 1

| ALS-in | ALS-in g/ha | Line A | Line B | Line C | Line WT |
|---|---|---|---|---|---|
| Foramsulfuron | 13 | 26.9% | 45.6% | 77.5% | 80.0% |
| Iodosulfuron-methyl-Na | 3.5 | 22.5% | 38.8% | 80.0% | 82.5% |
| Amidosulfuron | 15 | 6.3% | 37.5% | 51.9% | 73.1% |
| Thiencarbazone-methyl | 7.5 | 8.1% | 35.6% | 37.5% | 84.4% |
| Bisbyribac-Na | 50 | 17.5% | 38.1% | 71.7% | 80.0% |
| Metosulam | 15 | 13.1% | 40.6% | 69.4% | 79.4% |

According to the data shown in Table 1, it can clearly be demonstrated that the sugar beet plants of "Line A" were markedly more tolerant to the application of various ALS inhibitor herbicides, i.e. tolerance has been demonstrated to representative ALS inhibitor herbicides, whereas the conventional variety, i.e. the wild-type ("Line WT"), was significantly damaged under identical conditions.

Additionally, typical early phenotypes of each sugar beet plants were inspected after treatment with a mixture comprising thiencarbazone-methyl and foramsulfuron. A representative early phenotype of each Line is shown in FIG. 1 (FIG. 1).

FIG. 1 also demonstrates that the sugar beet plants particularly suitable for use in the context of the present invention ("Line A") show superior ALS inhibitor herbicide resistance, i.e. superior growth and less phytotoxic effects were observed in comparison to the other early phenotypes of "Line B", Line C" and "Line WT".

The invention claimed is:

1. A method for controlling unwanted vegetation in a *Beta vulgaris* plant growing area, comprising:
   (a) in the presence of one or more *Beta vulgaris* plants comprising a mutation in an endogenous ALS gene encoding an ALS protein containing an amino acid that is different from tryptophan at position 569 and an amino acid that is different from proline at position 188,
   (b) applying to the one or more *Beta vulgaris* plants one or more ALS inhibitor herbicides alone or in combination with one or more herbicides that does not belong to the class of ALS inhibitor herbicides (non-ALS inhibitor herbicides), and
   (c) wherein the applying of the herbicides as defined in (b)
      (i) takes place jointly or simultaneously, or
      (ii) takes place at different times and/or sequentially, as pre-emergence applications followed by post-emergence applications or early post-emergence applications followed by medium or late post-emergence applications.

2. The method according to claim 1, wherein the one or more ALS inhibitor herbicides is selected from the group consisting of: amidosulfuron [CAS RN 120923-37-7] (=A1-1); foramsulfuron [CAS RN 173159-57-4] (=A1-13); iodosulfuron-methyl-sodium [CAS RN 144550-36-7] (=A1-16); 2-iodo-N-[(4-methoxy-6-methyl-1,3,5-triazinyl)carbamoyl]benzene-sulfonamide (=A1-39); 2-iodo-N-[(4-methoxy-6-methyl-1,3,5-triazinyl)carbamoyl]benzene-sulfonamide sodium salt A1-41; compound A1-83 or its sodium salt (=A1-87); thiencarbazone-methyl [CAS RN 317815-83-1] (=A2-3); imazamox [CAS RN 114311-32-9] (=B1-2); and bispyribac-sodium [CAS RN 125401-92-5] (=C1-1).

3. The method according to claim 1, wherein amino acid of the ALS protein at position 569 is leucine.

4. The method according to claim 1, and wherein the one or more non-ALS inhibitor herbicides is applied and is selected from the group consisting of: desmedipham, ethofumesate, glufosinate, glufosinate-ammonium, glufosinate-P, glufosinate-P-ammonium, glufosinate-P-sodium, glyphosate, glyphosate-isopropylammonium, lenacil, metamitron, phenmedipham, phenmedipham-ethyl.

5. A method according to claim 1 for controlling unwanted vegetation, and wherein the one or more ALS inhibitor herbicides is selected from a group of the (sulfon)amides (group (A)) consisting of:
   a subgroup (A1) of the sulfonylureas, consisting of:
      amidosulfuron [CAS RN 120923-37-7] (=A1-1);
      azimsulfuron [CAS RN 120162-55-2] (=A1-2);
      bensulfuron-methyl [CAS RN 83055-99-6] (=A1-3);
      chlorimuron-ethyl [CAS RN 90982-32-4] (=A1-4);
      chlorsulfuron [CAS RN 64902-72-3] (=A1-5);
      cinosulfuron [CAS RN 94593-91-6] (=A1-6);
      cyclosulfamuron [CAS RN 136849-15-5] (=A1-7);
      ethametsulfuron-methyl [CAS RN 97780-06-8] (=A1-8);
      ethoxysulfuron [CAS RN 126801-58-9] (=A1-9);
      flazasulfuron [CAS RN 104040-78-0] (=A1-10);
      flucetosulfuron [CAS RN 412928-75-7] (=A1-11);
      flupyrsulfuron-methyl-sodium [CAS RN 144740-54-5] (=A1-12);
      foramsulfuron [CAS RN 173159-57-4] (=A1-13);
      halosulfuron-methyl [CAS RN 100784-20-1] (=A1-14);
      imazosulfuron [CAS RN 122548-33-8] (=A1-15);
      iodosulfuron-methyl-sodium [CAS RN 144550-36-7] (=A1-16);
      mesosulfuron-methyl [CAS RN 208465-21-8] (=A1-17);
      metsulfuron-methyl [CAS RN 74223-64-6] (=A1-18);
      monosulfuron [CAS RN 155860-63-2] (=A1-19);
      nicosulfuron [CAS RN 111991-09-4] (=A1-20);
      orthosulfamuron [CAS RN 213464-77-8] (=A1-21);
      oxasulfuron [CAS RN 144651-06-9] (=A1-22);
      primisulfuron-methyl [CAS RN 86209-51-0] (=A1-23);
      prosulfuron [CAS RN 94125-34-5] (=A1-24);
      pyrazosulfuron-ethyl [CAS RN 93697-74-6] (=A1-25);
      rimsulfuron [CAS RN 122931-48-0] (=A1-26);
      sulfometuron-methyl [CAS RN 74222-97-2] (=A1-27);
      sulfosulfuron [CAS RN 141776-32-1] (=A1-28);
      thifensulfuron-methyl [CAS RN 79277-27-3] (=A1-29);
      triasulfuron [CAS RN 82097-50-5] (=A1-30);
      tribenuron-methyl [CAS RN 101200-48-0] (=A1-31);
      trifloxysulfuron [CAS RN 145099-21-4] (sodium) (=A1-32);
      triflusulfuron-methyl [CAS RN 126535-15-7] (=A1-33);
      tritosulfuron [CAS RN 142469-14-5] (=A1-34);
      NC-330 [CAS RN 104770-29-8] (=A1-35);
      NC-620 [CAS RN 868680-84-6] (=A1-36);
      TH-547 [CAS RN 570415-88-2] (=A1-37);
      monosulfuron-methyl [CAS RN 175076-90-1] (=A1-38);
      2-iodo-N-[(4-methoxy-6-methyl-1,3,5-triazinyl)carbamoyl]benzene-sulfonamide (=A1-39);

a compound of formula (I)

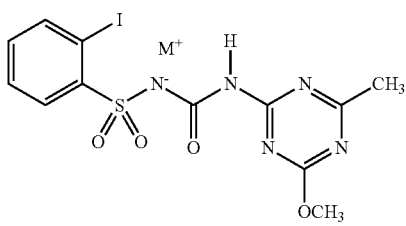

where M⁺ denotes the respective salt of the compound (I), comprising a lithium salt (=A1-40); sodium salt (=A1-41); potassium salt (=A1-42); magnesium salt (=A1-43); calcium salt (=A1-44); ammonium salt (=A1-45); methylammonium salt (=A1-46); dimethylammonium salt (=A1-47); tetramethylammonium salt (=A1-48); ethylammonium salt (=A1-49); diethylammonium salt (=A1-50); tetraethylammonium salt (=A1-51); propylammonium salt (=A1-52); tetrapropylammonium salt (=A1-53); isopropylammonium salt (=A1-54); diisopropylammonium salt (=A1-55); butylammonium salt (=A1-56); tetrabutylammonium salt (=A1-57); (2-hydroxyeth-1-yl)ammonium salt (=A1-58); bis-N,N-(2-hydroxyeth-1-yl) ammonium salt (=A1-59); tris-N,N,N-(2-hydroxyeth-1-yl)ammonium salt (=A1-60); 1-phenylethylammonium salt (=A1-61); 2-phenylethylammonium salt (=A1-62); trimethylsulfonium salt (=A1-63); trimethyloxonium salt (=A1-64); pyridinium salt (=A1-65); 2-methylpyridinium salt (=A1-66); 4-methylpyridinium salt (=A1-67); 2,4-dimethylpyridinium salt (=A1-68); 2,6-dimethylpyridinium salt (=A1-69); piperidinium salt (=A1-70); imidazolium salt (=A1-71); morpholinium salt (=A1-72); 1,5-diazabicyclo[4.3.0]non-7-enium salt (=A1-73); or 1,8-diazabicyclo[5.4.0]undec-7-enium salt (=A1-74);

or a compound of formula (II) or a salt thereof

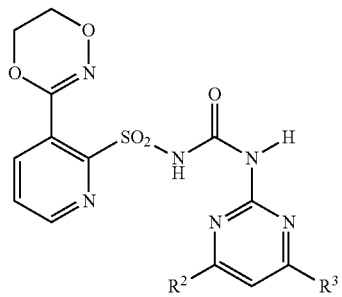

with R², and R³ having the meaning as defined in the below table

| Compound | R² | R³ |
|---|---|---|
| A1-75 | OCH₃ | OC₂H₅ |
| A1-76 | OCH₃ | CH₃ |
| A1-77 | OCH₃ | C₂H₅ |
| A1-78 | OCH₃ | CF₃ |

| Compound | R² | R³ |
|---|---|---|
| A1-79 | OCH₃ | OCF₂H |
| A1-80 | OCH₃ | NHCH₃ |
| A1-81 | OCH₃ | N(CH₃)₂ |
| A1-82 | OCH₃ | Cl |
| A1-83 | OCH₃ | OCH₃ |
| A1-84 | OC₂H₅ | OC₂H₅ |
| A1-85 | OC₂H₅ | CH₃ |
| A1-86 | OC₂H₅ | C₂H₅ | or a compound of formula (III) (=A1-87) or a sodium salt of compound (A1-83)

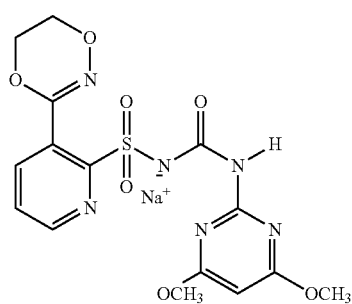

or a compound of formula (IV) (=A1-88) or a sodium salt of compound (A1-82)

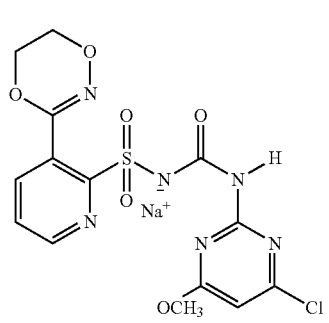

a subgroup of the sulfonylaminocarbonyltriazolinones (subgroup (A2)), consisting of:
flucarbazone-sodium [CAS RN 181274-17-9] (=A2-1);
propoxycarbazone-sodium [CAS RN 181274-15-7] (=A2-2);
thiencarbazone-methyl [CAS RN 317815-83-1] (=A2-3);
the subgroup of the triazolopyrimidines (subgroup (A3)), consisting of:
cloransulam-methyl [147150-35-4] (=A3-1);
diclosulam [CAS RN 145701-21-9] (=A3-2);
florasulam [CAS RN 145701-23-1] (=A3-3);
flumetsulam [CAS RN 98967-40-9] (=A3-4);
metosulam [CAS RN 139528-85-1] (=A3-5);
penoxsulam [CAS RN 219714-96-2] (=A3-6);
pyroxsulam [CAS RN 422556-08-9] (=A3-7);
a subgroup of the sulfonanilides (subgroup (A4)), consisting of:
one or more compounds or salts thereof from the group represented by formula (I):

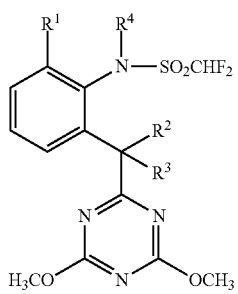
(V)
in which
R¹ is halogen,
R² is hydrogen and R³ is hydroxyl or
R² and R³ together with the carbon atom to which they are attached are a carbonyl group C=O and
R⁴ is hydrogen or methyl;
or compounds of the below given chemical structure (A4-1) to (A4-8)
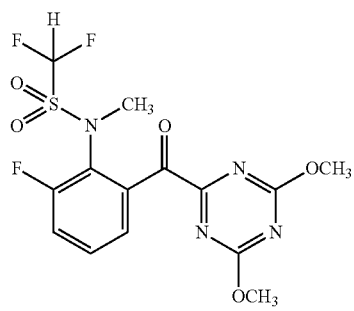
(A4-1)
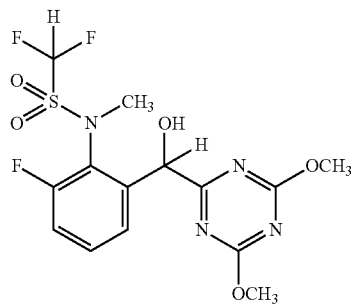
(A4-2)
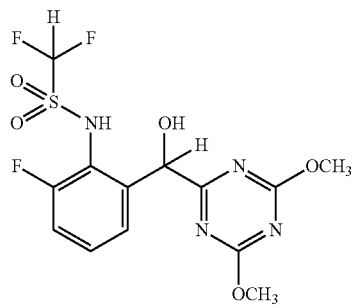
(A4-3)
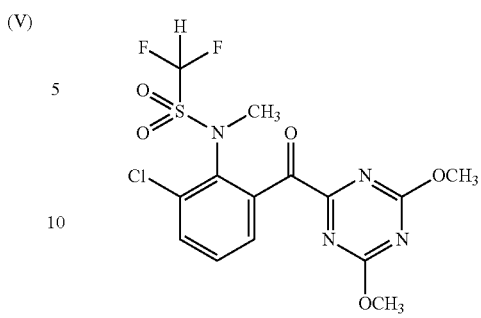
(A4-4)
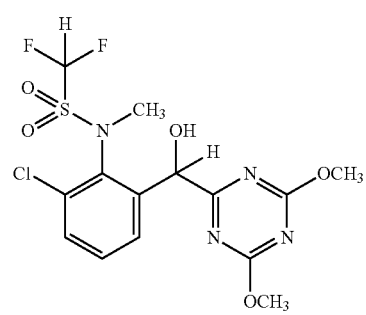
(A4-5)
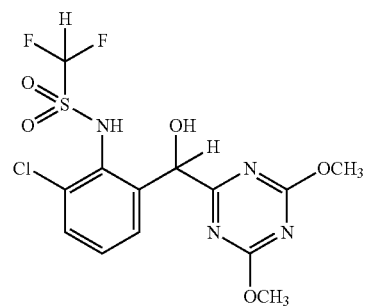
(A4-6)
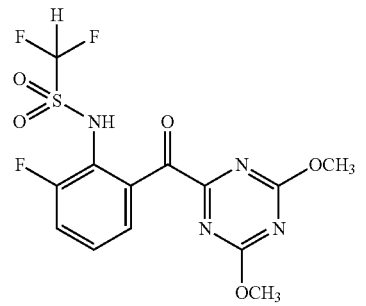
(A4-7)
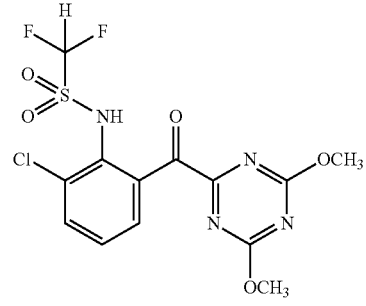
(A4-8)
a group of the imidazolinones (group (B1)), consisting of:
imazamethabenzmethyl [CAS RN 81405-85-8] (=B1-1);

imazamox [CAS RN 114311-32-9] (=B1-2);
imazapic [CAS RN 104098-48-8] (=B1-3);
imazapyr [CAS RN 81334-34-1] (=B1-4);
imazaquin [CAS RN 81335-37-7] (=B1-5);
imazethapyr [CAS RN 81335-77-5] (=B1-6);
SYP-298 [CAS RN 557064-77-4] (=B1-7);
SYP-300 [CAS RN 374718-10-2] (=B1-8);
a group of the pyrimidinyl(thio)benzoates (group (C)), consisting of:
  a subgroup of the pyrimidinyloxybenzoeacids (subgroup (C1)) consisting of:
  bispyribac-sodium [CAS RN 125401-92-5] (=C1-1);
  pyribenzoxim [CAS RN 168088-61-7] (=C1-2);
  pyriminobac-methyl [CAS RN 136191-64-5] (=C1-3);
  pyribambenz-isopropyl [CAS RN 420138-41-6] (=C1-4);
  pyribambenz-propyl [CAS RN 420138-40-5] (=C1-5);
  the subgroup of the pyrimidinylthiobenzoeacids (subgroup (C2)), consisting of:
  pyriftalid [CAS RN 135186-78-6] (=C2-1);
  pyrithiobac-sodium [CAS RN 123343-16-8] (=C2-2).

6. A method according to claim 1, and wherein the one or more ALS inhibitor herbicides is selected from the group consisting of:
amidosulfuron [CAS RN 120923-37-7] (=A1-1);
chlorimuron-ethyl [CAS RN 90982-32-4] (=A1-4);
ethametsulfuron-methyl [CAS RN 97780-06-8] (=A1-8);
ethoxysulfuron [CAS RN 126801-58-9] (=A1-9);
flupyrsulfuron-methyl-sodium [CAS RN 144740-54-5] (=A1-12);
foramsulfuron [CAS RN 173159-57-4] (=A1-13);
iodosulfuron-methyl-sodium [CAS RN 144550-36-7] (=A1-16);
mesosulfuron-methyl [CAS RN 208465-21-8] (=A1-17);
metsulfuron-methyl [CAS RN 74223-64-6] (=A1-18);
monosulfuron [CAS RN 155860-63-2] (=A1-19);
nicosulfuron [CAS RN 111991-09-4] (=A1-20);
sulfosulfuron [CAS RN 141776-32-1] (=A1-28);
thifensulfuron-methyl [CAS RN 79277-27-3] (=A1-29);
tribenuron-methyl [CAS RN 101200-48-0] (=A1-31);
2-iodo-N-[(4-methoxy-6-methyl-1,3,5-triazinyl)carbamoyl]benzene-sulfonamide (=A1-39);
2-iodo-N-[(4-methoxy-6-methyl-1,3,5-triazinyl)carbamoyl]benzene-sulfonamide sodium salt (=A1-41);
compound (A1-83) or sodium salt (=A1-87);
propoxycarbazone-sodium [CAS RN 181274-15-7] (=A2-2);
thiencarbazone-methyl [CAS RN 317815-83-1] (=A2-3);
florasulam [CAS RN 145701-23-1] (=A3-3);
metosulam [CAS RN 139528-85-1] (=A3-5);
pyroxsulam [CAS RN 422556-08-9] (=A3-7);
compound (A4-1);
compound (A4-2);
compound (A4-3);
imazamox [CAS RN 114311-32-9] (=B1-2); and
bispyribac-sodium [CAS RN 125401-92-5] (=C1-1).

7. A method according to claim 1, and wherein the one or more non-ALS inhibitor herbicides is applied and is selected from the group consisting of: chloridazon, clethodim, clodinafop, clodinafop-propargyl, clopyralid, cycloxydim, desmedipham, dimethenamid, dimethenamid-P, ethofumesate, fenoxaprop, fenoxaprop-P, fenoxaprop-ethyl, fenoxaprop-P-ethyl, fluazifop, fluazifop-P, fluazifop-butyl, fluazifop-P-butyl, glufosinate, glufosinate-ammonium, glufosinate-P, glufosinate-P-ammonium, glufosinate-P-sodium, glyphosate, glyphosate-isopropylammonium, haloxyfop, haloxyfop-P, haloxyfop-ethoxyethyl, haloxyfop-P-ethoxyethyl, haloxyfop-methyl, haloxyfop-P-methyl, lenacil, metamitro, phenmedipham, phenmedipham-ethyl, propaquizafop, quinmerac, quizalofop, quizalofop-ethyl, quizalofop-P, quizalofop-P-ethyl, quizalofop-P-tefuryl, sethoxydim.

8. A method according to claim 1, wherein the one or more *Beta vulgaris* plants is a deposit under NCIMB 42050.

9. The method according to claim 1, wherein in said (b), the one or more ALS inhibitor herbicides is applied alone.

10. The method according to claim 1, wherein the ALS inhibitor herbicide is foramsulfuron [CAS RN 173159-57-4] (=A1-13).

11. The method according to claim 1, wherein the ALS inhibitor herbicide is thiencarbazone-methyl [CAS RN 317815-83-1] (=A2-3).

12. The method according to claim 1, wherein the applying of the herbicides as defined in said (b) takes place jointly or simultaneously.

* * * * *

SEQUENCE LISTING

<160> NUMBER OF SEQ ID NOS: 8

<210> SEQ ID NO 1
<211> LENGTH: 1995
<212> TYPE: DNA
<213> ORGANISM: Beta vulgaris
<220> FEATURE:
<221> NAME/KEY: CDS
<222> LOCATION: (1)..(1995)
<223> OTHER INFORMATION: 4D6834 WT al1

<400> SEQUENCE: 1

```
atg gcg gct acc ttc aca aac cca aca ttt tcc cct tcc tca act cca        48
Met Ala Ala Thr Phe Thr Asn Pro Thr Phe Ser Pro Ser Ser Thr Pro
1               5                   10                  15 tta acc aaa acc cta aaa tcc caa tct tcc atc tct tca acc ctc ccc        96
Leu Thr Lys Thr Leu Lys Ser Gln Ser Ser Ile Ser Ser Thr Leu Pro
                20                  25                  30 ttt tcc acc cct ccc aaa acc cca act cca ctc ttt cac cgt ccc ctc       144
Phe Ser Thr Pro Pro Lys Thr Pro Thr Pro Leu Phe His Arg Pro Leu
            35                  40                  45 caa atc tca tcc tcc caa tcc cac aaa tca tcc gcc att aaa aca caa       192
Gln Ile Ser Ser Ser Gln Ser His Lys Ser Ser Ala Ile Lys Thr Gln
        50                  55                  60 act caa gca cct tct tct cca gct att gaa gat tca tct ttc gtt tct       240
Thr Gln Ala Pro Ser Ser Pro Ala Ile Glu Asp Ser Ser Phe Val Ser
65                  70                  75                  80 cga ttt ggc cct gat gaa ccc aga aaa ggg tcc gat gtc ctc gtt gaa       288
Arg Phe Gly Pro Asp Glu Pro Arg Lys Gly Ser Asp Val Leu Val Glu
                85                  90                  95 gct ctt gag cgt gaa ggt gtt acc aat gtg ttt gct tac cct ggt ggt       336
Ala Leu Glu Arg Glu Gly Val Thr Asn Val Phe Ala Tyr Pro Gly Gly
                100                 105                 110 gca tct atg gaa atc cac caa gct ctc aca cgc tct aaa acc atc cgc       384
Ala Ser Met Glu Ile His Gln Ala Leu Thr Arg Ser Lys Thr Ile Arg
            115                 120                 125 aat gtc ctc cct cgc cat gaa caa ggc ggg gtt ttc gcc gcc gag gga       432
Asn Val Leu Pro Arg His Glu Gln Gly Gly Val Phe Ala Ala Glu Gly
        130                 135                 140 tat gct aga gct act gga aag gtt ggt gtc tgc att gcg act tct ggt       480
Tyr Ala Arg Ala Thr Gly Lys Val Gly Val Cys Ile Ala Thr Ser Gly
145                 150                 155                 160 cct ggt gct acc aac ctc gta tca ggt ctt gct gac gct ctc ctt gat       528
Pro Gly Ala Thr Asn Leu Val Ser Gly Leu Ala Asp Ala Leu Leu Asp
                165                 170                 175 tct gtc cct ctt gtt gcc atc act ggc caa gtt cca cgc cgt atg att       576
Ser Val Pro Leu Val Ala Ile Thr Gly Gln Val Pro Arg Arg Met Ile
            180                 185                 190 ggc act gat gct ttt cag gag act cca att gtt gag gtg aca agg tct       624
Gly Thr Asp Ala Phe Gln Glu Thr Pro Ile Val Glu Val Thr Arg Ser
        195                 200                 205 att act aag cat aat tat tta gtt ttg gat gta gag gat att cct aga       672
Ile Thr Lys His Asn Tyr Leu Val Leu Asp Val Glu Asp Ile Pro Arg
    210                 215                 220 att gtt aag gaa gcc ttt ttt tta gct aat tct ggt agg cct gga cct       720
Ile Val Lys Glu Ala Phe Phe Leu Ala Asn Ser Gly Arg Pro Gly Pro
225                 230                 235                 240 gtt ttg att gat ctt cct aaa gat att cag cag caa ttg gtt gtt cct       768
Val Leu Ile Asp Leu Pro Lys Asp Ile Gln Gln Gln Leu Val Val Pro
                245                 250                 255 gat tgg gat agg cct ttt aag ttg ggt ggg tat atg tct agg ctg cca       816
Asp Trp Asp Arg Pro Phe Lys Leu Gly Gly Tyr Met Ser Arg Leu Pro
```

```
                Asp Trp Asp Arg Pro Phe Lys Leu Gly Gly Tyr Met Ser Arg Leu Pro
                        260                 265                 270 aag tcc aag ttt tcg acg aat gag gtt gga ctt ctt gag cag att gtg          864
Lys Ser Lys Phe Ser Thr Asn Glu Val Gly Leu Leu Glu Gln Ile Val
            275                 280                 285 agg ttg atg agt gag tcg aag aag cct gtc ttg tat gtg gga ggt ggg          912
Arg Leu Met Ser Glu Ser Lys Lys Pro Val Leu Tyr Val Gly Gly Gly
        290                 295                 300 tgt ttg aat tct agt gag gag ttg agg aga ttt gtt gag ttg aca ggg          960
Cys Leu Asn Ser Ser Glu Glu Leu Arg Arg Phe Val Glu Leu Thr Gly
305                 310                 315                 320 att ccg gtg gct agt act ttg atg ggg ttg ggg tct tac cct tgt aat         1008
Ile Pro Val Ala Ser Thr Leu Met Gly Leu Gly Ser Tyr Pro Cys Asn
                325                 330                 335 gat gaa ctg tct ctt cat atg ttg ggg atg cac ggg act gtt tat gcc         1056
Asp Glu Leu Ser Leu His Met Leu Gly Met His Gly Thr Val Tyr Ala
            340                 345                 350 aat tat gcg gtg gat aag gcg gat ttg ttg ctt gct ttc ggg gtt agg         1104
Asn Tyr Ala Val Asp Lys Ala Asp Leu Leu Leu Ala Phe Gly Val Arg
        355                 360                 365 ttt gat gat cgt gtg acc ggg aag ctc gag gcg ttt gct agc cgt gct         1152
Phe Asp Asp Arg Val Thr Gly Lys Leu Glu Ala Phe Ala Ser Arg Ala
370                 375                 380 aag att gtg cat att gat att gac tct gct gag att ggg aag aac aag         1200
Lys Ile Val His Ile Asp Ile Asp Ser Ala Glu Ile Gly Lys Asn Lys
385                 390                 395                 400 cag ccc cat gtg tcc att tgt gct gat gtt aaa ttg gca ttg cgg ggt         1248
Gln Pro His Val Ser Ile Cys Ala Asp Val Lys Leu Ala Leu Arg Gly
                405                 410                 415 atg aat aag att ctg gag tct aga ata ggg aag ctg aat ttg gat ttc         1296
Met Asn Lys Ile Leu Glu Ser Arg Ile Gly Lys Leu Asn Leu Asp Phe
            420                 425                 430 tcc aag tgg aga gaa gaa tta ggt gag cag aag aag gaa ttc cca ctg         1344
Ser Lys Trp Arg Glu Glu Leu Gly Glu Gln Lys Lys Glu Phe Pro Leu
        435                 440                 445 agt ttt aag aca ttt ggg gat gca att cct cca caa tat gcc att cag         1392
Ser Phe Lys Thr Phe Gly Asp Ala Ile Pro Pro Gln Tyr Ala Ile Gln
450                 455                 460 gtg ctt gat gag ttg acc aat ggt aat gct att ata agt act ggt gtt         1440
Val Leu Asp Glu Leu Thr Asn Gly Asn Ala Ile Ile Ser Thr Gly Val
465                 470                 475                 480 ggg cag cac caa atg tgg gct gcg cag cat tac aag tac aga aac cct         1488
Gly Gln His Gln Met Trp Ala Ala Gln His Tyr Lys Tyr Arg Asn Pro
                485                 490                 495 cgc caa tgg ctg acc tct ggt ggg ttg ggg gct atg ggg ttt ggg cta         1536
Arg Gln Trp Leu Thr Ser Gly Gly Leu Gly Ala Met Gly Phe Gly Leu
            500                 505                 510 cca gcc gcc att gga gct gca gtt gct cga cca gat gca gtg gtt gtc         1584
Pro Ala Ala Ile Gly Ala Ala Val Ala Arg Pro Asp Ala Val Val Val
        515                 520                 525 gat att gat ggg gat ggc agt ttt att atg aat gtt caa gag ttg gct         1632
Asp Ile Asp Gly Asp Gly Ser Phe Ile Met Asn Val Gln Glu Leu Ala
530                 535                 540 aca att agg gtg gaa aat ctc cca gtt aag ata atg ctg cta aac aat         1680
Thr Ile Arg Val Glu Asn Leu Pro Val Lys Ile Met Leu Leu Asn Asn
545                 550                 555                 560 caa cat tta ggt atg gtt gtc caa tgg gaa gat agg ttc tat aaa gct         1728
Gln His Leu Gly Met Val Val Gln Trp Glu Asp Arg Phe Tyr Lys Ala
                565                 570                 575
```

```
aac cgg gca cat aca tac ctt gga aac cct tcc aaa tct gct gat atc    1776
Asn Arg Ala His Thr Tyr Leu Gly Asn Pro Ser Lys Ser Ala Asp Ile
            580                 585                 590 ttc cct gat atg ctc aaa ttc gct gag gca tgt gat att cct tct gcc    1824
Phe Pro Asp Met Leu Lys Phe Ala Glu Ala Cys Asp Ile Pro Ser Ala
        595                 600                 605 cgt gtt agc aac gtg gct gat ttg agg gcc gcc att caa aca atg ttg    1872
Arg Val Ser Asn Val Ala Asp Leu Arg Ala Ala Ile Gln Thr Met Leu
    610                 615                 620 gat act cca ggg ccg tac ctg ctc gat gtg att gta ccg cat caa gag    1920
Asp Thr Pro Gly Pro Tyr Leu Leu Asp Val Ile Val Pro His Gln Glu
625                 630                 635                 640 cat gtg ttg cct atg att cca agt ggt gcc ggt ttc aag gat acc att    1968
His Val Leu Pro Met Ile Pro Ser Gly Ala Gly Phe Lys Asp Thr Ile
                645                 650                 655 aca gag ggt gat gga aga acc tct taa                                1995
Thr Glu Gly Asp Gly Arg Thr Ser
            660

<210> SEQ ID NO 2
<211> LENGTH: 664
<212> TYPE: PRT
<213> ORGANISM: Beta vulgaris

<400> SEQUENCE: 2

Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
    130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Pro Arg Arg Met Ile
            180                 185                 190

Gly Thr Asp Ala Phe Gln Glu Thr Pro Ile Val Glu Val Thr Arg Ser
        195                 200                 205

Ile Thr Lys His Asn Tyr Leu Val Leu Asp Val Glu Asp Ile Pro Arg
    210                 215                 220

Ile Val Lys Glu Ala Phe Phe Leu Ala Asn Ser Gly Arg Pro Gly Pro
225                 230                 235                 240

Val Leu Ile Asp Leu Pro Lys Asp Ile Gln Gln Gln Leu Val Val Pro
                245                 250                 255
```

```
Asp Trp Asp Arg Pro Phe Lys Leu Gly Gly Tyr Met Ser Arg Leu Pro
            260                 265                 270

Lys Ser Lys Phe Ser Thr Asn Glu Val Gly Leu Leu Glu Gln Ile Val
        275                 280                 285

Arg Leu Met Ser Glu Ser Lys Lys Pro Val Leu Tyr Val Gly Gly Gly
    290                 295                 300

Cys Leu Asn Ser Ser Glu Glu Leu Arg Arg Phe Val Glu Leu Thr Gly
305                 310                 315                 320

Ile Pro Val Ala Ser Thr Leu Met Gly Leu Gly Ser Tyr Pro Cys Asn
                325                 330                 335

Asp Glu Leu Ser Leu His Met Leu Gly Met His Gly Thr Val Tyr Ala
                340                 345                 350

Asn Tyr Ala Val Asp Lys Ala Asp Leu Leu Ala Phe Gly Val Arg
        355                 360                 365

Phe Asp Asp Arg Val Thr Gly Lys Leu Glu Ala Phe Ala Ser Arg Ala
    370                 375                 380

Lys Ile Val His Ile Asp Ile Asp Ser Ala Glu Ile Gly Lys Asn Lys
385                 390                 395                 400

Gln Pro His Val Ser Ile Cys Ala Asp Val Lys Leu Ala Leu Arg Gly
                405                 410                 415

Met Asn Lys Ile Leu Glu Ser Arg Ile Gly Lys Leu Asn Leu Asp Phe
            420                 425                 430

Ser Lys Trp Arg Glu Glu Leu Gly Glu Gln Lys Lys Glu Phe Pro Leu
        435                 440                 445

Ser Phe Lys Thr Phe Gly Asp Ala Ile Pro Pro Gln Tyr Ala Ile Gln
    450                 455                 460

Val Leu Asp Glu Leu Thr Asn Gly Asn Ala Ile Ile Ser Thr Gly Val
465                 470                 475                 480

Gly Gln His Gln Met Trp Ala Ala Gln His Tyr Lys Tyr Arg Asn Pro
                485                 490                 495

Arg Gln Trp Leu Thr Ser Gly Gly Leu Gly Ala Met Gly Phe Gly Leu
            500                 505                 510

Pro Ala Ala Ile Gly Ala Ala Val Ala Arg Pro Asp Ala Val Val Val
        515                 520                 525

Asp Ile Asp Gly Asp Gly Ser Phe Ile Met Asn Val Gln Glu Leu Ala
    530                 535                 540

Thr Ile Arg Val Glu Asn Leu Pro Val Lys Ile Met Leu Leu Asn Asn
545                 550                 555                 560

Gln His Leu Gly Met Val Val Gln Trp Glu Asp Arg Phe Tyr Lys Ala
                565                 570                 575

Asn Arg Ala His Thr Tyr Leu Gly Asn Pro Ser Lys Ser Ala Asp Ile
            580                 585                 590

Phe Pro Asp Met Leu Lys Phe Ala Glu Ala Cys Asp Ile Pro Ser Ala
        595                 600                 605

Arg Val Ser Asn Val Ala Asp Leu Arg Ala Ala Ile Gln Thr Met Leu
    610                 615                 620

Asp Thr Pro Gly Pro Tyr Leu Leu Asp Val Ile Val Pro His Gln Glu
625                 630                 635                 640

His Val Leu Pro Met Ile Pro Ser Gly Ala Gly Phe Lys Asp Thr Ile
                645                 650                 655

Thr Glu Gly Asp Gly Arg Thr Ser
            660
```

```
<210> SEQ ID NO 3
<211> LENGTH: 1995
<212> TYPE: DNA
<213> ORGANISM: Beta vulgaris
<220> FEATURE:
<221> NAME/KEY: misc_feature
<222> LOCATION: (1)..(1994)
<223> OTHER INFORMATION: 4D6834 W574
<220> FEATURE:
<221> NAME/KEY: CDS
<222> LOCATION: (1)..(1995)

<400> SEQUENCE: 3
```

| | | | | | | | | | | | | | | | | |
|---|---|---|---|---|---|---|---|---|---|---|---|---|---|---|---|---|
| atg | gcg | gct | acc | ttc | aca | aac | cca | aca | ttt | tcc | cct | tcc | tca | act | cca | 48 |
| Met | Ala | Ala | Thr | Phe | Thr | Asn | Pro | Thr | Phe | Ser | Pro | Ser | Ser | Thr | Pro | |
| 1 | | | | 5 | | | | | 10 | | | | | 15 | | |
| tta | acc | aaa | acc | cta | aaa | tcc | caa | tct | tcc | atc | tct | tca | acc | ctc | ccc | 96 |
| Leu | Thr | Lys | Thr | Leu | Lys | Ser | Gln | Ser | Ser | Ile | Ser | Ser | Thr | Leu | Pro | |
| | | | 20 | | | | | 25 | | | | | 30 | | | |
| ttt | tcc | acc | cct | ccc | aaa | acc | cca | act | cca | ctc | ttt | cac | cgt | ccc | ctc | 144 |
| Phe | Ser | Thr | Pro | Pro | Lys | Thr | Pro | Thr | Pro | Leu | Phe | His | Arg | Pro | Leu | |
| | | 35 | | | | | 40 | | | | | 45 | | | | |
| caa | atc | tca | tcc | tcc | caa | tcc | cac | aaa | tca | tcc | gcc | att | aaa | aca | caa | 192 |
| Gln | Ile | Ser | Ser | Ser | Gln | Ser | His | Lys | Ser | Ser | Ala | Ile | Lys | Thr | Gln | |
| | 50 | | | | | 55 | | | | | 60 | | | | | |
| act | caa | gca | cct | tct | tct | cca | gct | att | gaa | gat | tca | tct | ttc | gtt | tct | 240 |
| Thr | Gln | Ala | Pro | Ser | Ser | Pro | Ala | Ile | Glu | Asp | Ser | Ser | Phe | Val | Ser | |
| 65 | | | | | 70 | | | | | 75 | | | | | 80 | |
| cga | ttt | ggc | cct | gat | gaa | ccc | aga | aaa | ggg | tcc | gat | gtc | ctc | gtt | gaa | 288 |
| Arg | Phe | Gly | Pro | Asp | Glu | Pro | Arg | Lys | Gly | Ser | Asp | Val | Leu | Val | Glu | |
| | | | | 85 | | | | | 90 | | | | | 95 | | |
| gct | ctt | gag | cgt | gaa | ggt | gtt | acc | aat | gtg | ttt | gct | tac | cct | ggt | ggt | 336 |
| Ala | Leu | Glu | Arg | Glu | Gly | Val | Thr | Asn | Val | Phe | Ala | Tyr | Pro | Gly | Gly | |
| | | | 100 | | | | | 105 | | | | | 110 | | | |
| gca | tct | atg | gaa | atc | cac | caa | gct | ctc | aca | cgc | tct | aaa | acc | atc | cgc | 384 |
| Ala | Ser | Met | Glu | Ile | His | Gln | Ala | Leu | Thr | Arg | Ser | Lys | Thr | Ile | Arg | |
| | 115 | | | | | 120 | | | | | 125 | | | | | |
| aat | gtc | ctc | cct | cgc | cat | gaa | caa | ggc | ggg | gtt | ttc | gcc | gcc | gag | gga | 432 |
| Asn | Val | Leu | Pro | Arg | His | Glu | Gln | Gly | Gly | Val | Phe | Ala | Ala | Glu | Gly | |
| 130 | | | | | 135 | | | | | 140 | | | | | | |
| tat | gct | aga | gct | act | gga | aag | gtt | ggt | gtc | tgc | att | gcg | act | tct | ggt | 480 |
| Tyr | Ala | Arg | Ala | Thr | Gly | Lys | Val | Gly | Val | Cys | Ile | Ala | Thr | Ser | Gly | |
| 145 | | | | | 150 | | | | | 155 | | | | | 160 | |
| cct | ggt | gct | acc | aac | ctc | gta | tca | ggt | ctt | gct | gac | gct | ctc | ctt | gat | 528 |
| Pro | Gly | Ala | Thr | Asn | Leu | Val | Ser | Gly | Leu | Ala | Asp | Ala | Leu | Leu | Asp | |
| | | | | 165 | | | | | 170 | | | | | 175 | | |
| tct | gtc | cct | ctt | gtt | gcc | atc | act | ggc | caa | gtt | cca | cgc | cgt | atg | att | 576 |
| Ser | Val | Pro | Leu | Val | Ala | Ile | Thr | Gly | Gln | Val | Pro | Arg | Arg | Met | Ile | |
| | | | 180 | | | | | 185 | | | | | 190 | | | |
| ggc | act | gat | gct | ttt | cag | gag | act | cca | att | gtt | gag | gtg | aca | agg | tct | 624 |
| Gly | Thr | Asp | Ala | Phe | Gln | Glu | Thr | Pro | Ile | Val | Glu | Val | Thr | Arg | Ser | |
| | 195 | | | | | 200 | | | | | 205 | | | | | |
| att | act | aag | cat | aat | tat | tta | gtt | ttg | gat | gta | gag | gat | att | cct | aga | 672 |
| Ile | Thr | Lys | His | Asn | Tyr | Leu | Val | Leu | Asp | Val | Glu | Asp | Ile | Pro | Arg | |
| 210 | | | | | 215 | | | | | 220 | | | | | | |
| att | gtt | aag | gaa | gcc | ttt | ttt | tta | gct | aat | tct | ggt | agg | cct | gga | cct | 720 |
| Ile | Val | Lys | Glu | Ala | Phe | Phe | Leu | Ala | Asn | Ser | Gly | Arg | Pro | Gly | Pro | |
| 225 | | | | | 230 | | | | | 235 | | | | | 240 | |
| gtt | ttg | att | gat | ctt | cct | aaa | gat | att | cag | cag | caa | ttg | gtt | gtt | cct | 768 |
| Val | Leu | Ile | Asp | Leu | Pro | Lys | Asp | Ile | Gln | Gln | Gln | Leu | Val | Val | Pro | |
| | | | | 245 | | | | | 250 | | | | | 255 | | |

```
gat tgg gat agg cct ttt aag ttg ggt ggg tat atg tct agg ctg cca    816
Asp Trp Asp Arg Pro Phe Lys Leu Gly Gly Tyr Met Ser Arg Leu Pro
        260             265             270 aag tcc aag ttt tcg acg aat gag gtt gga ctt ctt gag cag att gtg    864
Lys Ser Lys Phe Ser Thr Asn Glu Val Gly Leu Leu Glu Gln Ile Val
            275             280             285 agg ttg atg agt gag tcg aag aag cct gtc ttg tat gtg gga ggt ggg    912
Arg Leu Met Ser Glu Ser Lys Lys Pro Val Leu Tyr Val Gly Gly Gly
        290             295             300 tgt ttg aat tct agt gag gag ttg agg aga ttt gtt gag ttg aca ggg    960
Cys Leu Asn Ser Ser Glu Glu Leu Arg Arg Phe Val Glu Leu Thr Gly
305             310             315             320 att ccg gtg gct agt act ttg atg ggg ttg ggg tct tac cct tgt aat   1008
Ile Pro Val Ala Ser Thr Leu Met Gly Leu Gly Ser Tyr Pro Cys Asn
                325             330             335 gat gaa ctg tct ctt cat atg ttg ggg atg cac ggg act gtt tat gcc   1056
Asp Glu Leu Ser Leu His Met Leu Gly Met His Gly Thr Val Tyr Ala
        340             345             350 aat tat gcg gtg gat aag gcg gat ttg ttg ctt gct ttc ggg gtt agg   1104
Asn Tyr Ala Val Asp Lys Ala Asp Leu Leu Leu Ala Phe Gly Val Arg
            355             360             365 ttt gat gat cgt gtg acc ggg aag ctc gag gcg ttt gct agc cgt gct   1152
Phe Asp Asp Arg Val Thr Gly Lys Leu Glu Ala Phe Ala Ser Arg Ala
370             375             380 aag att gtg cat att gat att gac tct gct gag att ggg aag aac aag   1200
Lys Ile Val His Ile Asp Ile Asp Ser Ala Glu Ile Gly Lys Asn Lys
385             390             395             400 cag ccc cat gtg tcc att tgt gct gat gtt aaa ttg gca ttg cgg ggt   1248
Gln Pro His Val Ser Ile Cys Ala Asp Val Lys Leu Ala Leu Arg Gly
                405             410             415 atg aat aag att ctg gag tct aga ata ggg aag ctg aat ttg gat ttc   1296
Met Asn Lys Ile Leu Glu Ser Arg Ile Gly Lys Leu Asn Leu Asp Phe
        420             425             430 tcc aag tgg aga gaa gaa tta ggt gag cag aag aag gaa ttc cca ctg   1344
Ser Lys Trp Arg Glu Glu Leu Gly Glu Gln Lys Lys Glu Phe Pro Leu
            435             440             445 agt ttt aag aca ttt ggg gat gca att cct cca caa tat gcc att cag   1392
Ser Phe Lys Thr Phe Gly Asp Ala Ile Pro Pro Gln Tyr Ala Ile Gln
450             455             460 gtg ctt gat gag ttg acc aat ggt aat gct att ata agt act ggt gtt   1440
Val Leu Asp Glu Leu Thr Asn Gly Asn Ala Ile Ile Ser Thr Gly Val
465             470             475             480 ggg cag cac caa atg tgg gct gcg cag cat tac aag tac aga aac cct   1488
Gly Gln His Gln Met Trp Ala Ala Gln His Tyr Lys Tyr Arg Asn Pro
                485             490             495 cgc caa tgg ctg acc tct ggt ggg ttg ggg gct atg ggg ttt ggg cta   1536
Arg Gln Trp Leu Thr Ser Gly Gly Leu Gly Ala Met Gly Phe Gly Leu
        500             505             510 cca gcc gcc att gga gct gca gtt gct cga cca gat gca gtg gtt gtc   1584
Pro Ala Ala Ile Gly Ala Ala Val Ala Arg Pro Asp Ala Val Val Val
            515             520             525 gat att gat ggg gat ggc agt ttt att atg aat gtt caa gag ttg gct   1632
Asp Ile Asp Gly Asp Gly Ser Phe Ile Met Asn Val Gln Glu Leu Ala
530             535             540 aca att agg gtg gaa aat ctc cca gtt aag ata atg ctg cta aac aat   1680
Thr Ile Arg Val Glu Asn Leu Pro Val Lys Ile Met Leu Leu Asn Asn
545             550             555             560 caa cat tta ggt atg gtt gtc caa ttg gaa gat agg ttc tat aaa gct   1728
Gln His Leu Gly Met Val Val Gln Leu Glu Asp Arg Phe Tyr Lys Ala
                565             570             575
```

-continued

```
aac cgg gca cat aca tac ctt gga aac cct tcc aaa tct gct gat atc     1776
Asn Arg Ala His Thr Tyr Leu Gly Asn Pro Ser Lys Ser Ala Asp Ile
            580                 585                 590 ttc cct gat atg ctc aaa ttc gct gag gca tgt gat att cct tct gcc     1824
Phe Pro Asp Met Leu Lys Phe Ala Glu Ala Cys Asp Ile Pro Ser Ala
        595                 600                 605 cgt gtt agc aac gtg gct gat ttg agg gcc gcc att caa aca atg ttg     1872
Arg Val Ser Asn Val Ala Asp Leu Arg Ala Ala Ile Gln Thr Met Leu
    610                 615                 620 gat act cca ggg ccg tac ctg ctc gat gtg att gta ccg cat caa gag     1920
Asp Thr Pro Gly Pro Tyr Leu Leu Asp Val Ile Val Pro His Gln Glu
625                 630                 635                 640 cat gtg ttg cct atg att cca agt ggt gcc ggt ttc aag gat acc att     1968
His Val Leu Pro Met Ile Pro Ser Gly Ala Gly Phe Lys Asp Thr Ile
                645                 650                 655 aca gag ggt gat gga aga acc tct taa                                 1995
Thr Glu Gly Asp Gly Arg Thr Ser
                660
```

<210> SEQ ID NO 4
<211> LENGTH: 664
<212> TYPE: PRT
<213> ORGANISM: Beta vulgaris

<400> SEQUENCE: 4

Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
    130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Pro Arg Arg Met Ile
            180                 185                 190

Gly Thr Asp Ala Phe Gln Glu Thr Pro Ile Val Glu Val Thr Arg Ser
        195                 200                 205

Ile Thr Lys His Asn Tyr Leu Val Asp Val Glu Asp Ile Pro Arg
    210                 215                 220

Ile Val Lys Glu Ala Phe Phe Leu Ala Asn Ser Gly Arg Pro Gly Pro
225                 230                 235                 240

Val Leu Ile Asp Leu Pro Lys Asp Ile Gln Gln Gln Leu Val Val Pro

```
                245                 250                 255
Asp Trp Asp Arg Pro Phe Lys Leu Gly Gly Tyr Met Ser Arg Leu Pro
            260                 265                 270
Lys Ser Lys Phe Ser Thr Asn Glu Val Gly Leu Leu Glu Gln Ile Val
            275                 280                 285
Arg Leu Met Ser Glu Ser Lys Lys Pro Val Leu Tyr Val Gly Gly Gly
            290                 295                 300
Cys Leu Asn Ser Ser Glu Glu Leu Arg Arg Phe Val Glu Leu Thr Gly
305                 310                 315                 320
Ile Pro Val Ala Ser Thr Leu Met Gly Leu Gly Ser Tyr Pro Cys Asn
                325                 330                 335
Asp Glu Leu Ser Leu His Met Leu Gly Met His Gly Thr Val Tyr Ala
            340                 345                 350
Asn Tyr Ala Val Asp Lys Ala Asp Leu Leu Ala Phe Gly Val Arg
            355                 360                 365
Phe Asp Asp Arg Val Thr Gly Lys Leu Glu Ala Phe Ala Ser Arg Ala
        370                 375                 380
Lys Ile Val His Ile Asp Ile Asp Ser Ala Glu Ile Gly Lys Asn Lys
385                 390                 395                 400
Gln Pro His Val Ser Ile Cys Ala Asp Val Lys Leu Ala Leu Arg Gly
                405                 410                 415
Met Asn Lys Ile Leu Glu Ser Arg Ile Gly Lys Leu Asn Leu Asp Phe
            420                 425                 430
Ser Lys Trp Arg Glu Glu Leu Gly Glu Gln Lys Lys Glu Phe Pro Leu
            435                 440                 445
Ser Phe Lys Thr Phe Gly Asp Ala Ile Pro Pro Gln Tyr Ala Ile Gln
        450                 455                 460
Val Leu Asp Glu Leu Thr Asn Gly Asn Ala Ile Ile Ser Thr Gly Val
465                 470                 475                 480
Gly Gln His Gln Met Trp Ala Ala Gln His Tyr Lys Tyr Arg Asn Pro
                485                 490                 495
Arg Gln Trp Leu Thr Ser Gly Gly Leu Gly Ala Met Gly Phe Gly Leu
            500                 505                 510
Pro Ala Ala Ile Gly Ala Ala Val Ala Arg Pro Asp Ala Val Val
            515                 520                 525
Asp Ile Asp Gly Asp Gly Ser Phe Ile Met Asn Val Gln Glu Leu Ala
        530                 535                 540
Thr Ile Arg Val Glu Asn Leu Pro Val Lys Ile Met Leu Leu Asn Asn
545                 550                 555                 560
Gln His Leu Gly Met Val Val Gln Leu Glu Asp Arg Phe Tyr Lys Ala
                565                 570                 575
Asn Arg Ala His Thr Tyr Leu Gly Asn Pro Ser Lys Ser Ala Asp Ile
            580                 585                 590
Phe Pro Asp Met Leu Lys Phe Ala Glu Ala Cys Asp Ile Pro Ser Ala
            595                 600                 605
Arg Val Ser Asn Val Ala Asp Leu Arg Ala Ala Ile Gln Thr Met Leu
        610                 615                 620
Asp Thr Pro Gly Pro Tyr Leu Leu Asp Val Ile Val Pro His Gln Glu
625                 630                 635                 640
His Val Leu Pro Met Ile Pro Ser Gly Ala Gly Phe Lys Asp Thr Ile
                645                 650                 655
Thr Glu Gly Asp Gly Arg Thr Ser
            660
```

-continued

```
<210> SEQ ID NO 5
<211> LENGTH: 1995
<212> TYPE: DNA
<213> ORGANISM: Beta vulgaris
<220> FEATURE:
<221> NAME/KEY: misc_feature
<222> LOCATION: (1)..(1994)
<223> OTHER INFORMATION: Pro Mutant
<220> FEATURE:
<221> NAME/KEY: CDS
<222> LOCATION: (1)..(1995)

<400> SEQUENCE: 5 atg gcg gct acc ttc aca aac cca aca ttt tcc cct tcc tca act cca      48
Met Ala Ala Thr Phe Thr Asn Pro Thr Phe Ser Pro Ser Ser Thr Pro
1               5                   10                  15 tta acc aaa acc cta aaa tcc caa tct tcc atc tct tca acc ctc ccc      96
Leu Thr Lys Thr Leu Lys Ser Gln Ser Ser Ile Ser Ser Thr Leu Pro
            20                  25                  30 ttt tcc acc cct ccc aaa acc cca act cca ctc ttt cac cgt ccc ctc     144
Phe Ser Thr Pro Pro Lys Thr Pro Thr Pro Leu Phe His Arg Pro Leu
        35                  40                  45 caa atc tca tcc tcc caa tcc cac aaa tca tcc gcc att aaa aca caa     192
Gln Ile Ser Ser Ser Gln Ser His Lys Ser Ser Ala Ile Lys Thr Gln
50                  55                  60 act caa gca cct tct tct cca gct att gaa gat tca tct ttc gtt tct     240
Thr Gln Ala Pro Ser Ser Pro Ala Ile Glu Asp Ser Ser Phe Val Ser
65                  70                  75                  80 cga ttt ggc cct gat gaa ccc aga aaa ggg tcc gat gtc ctc gtt gaa     288
Arg Phe Gly Pro Asp Glu Pro Arg Lys Gly Ser Asp Val Leu Val Glu
                85                  90                  95 gct ctt gag cgt gaa ggt gtt acc aat gtg ttt gct tac cct ggt ggt     336
Ala Leu Glu Arg Glu Gly Val Thr Asn Val Phe Ala Tyr Pro Gly Gly
            100                 105                 110 gca tct atg gaa atc cac caa gct ctc aca cgc tct aaa acc atc cgc     384
Ala Ser Met Glu Ile His Gln Ala Leu Thr Arg Ser Lys Thr Ile Arg
        115                 120                 125 aat gtc ctc cct cgc cat gaa caa ggc ggg gtt ttc gcc gcc gag gga     432
Asn Val Leu Pro Arg His Glu Gln Gly Gly Val Phe Ala Ala Glu Gly
130                 135                 140 tat gct aga gct act gga aag gtt ggt gtc tgc att gcg act tct ggt     480
Tyr Ala Arg Ala Thr Gly Lys Val Gly Val Cys Ile Ala Thr Ser Gly
145                 150                 155                 160 cct ggt gct acc aac ctc gta tca ggt ctt gct gac gct ctc ctt gat     528
Pro Gly Ala Thr Asn Leu Val Ser Gly Leu Ala Asp Ala Leu Leu Asp
                165                 170                 175 tct gtc cct ctt gtt gcc atc act ggc caa gtt tca cgc cgt atg att     576
Ser Val Pro Leu Val Ala Ile Thr Gly Gln Val Ser Arg Arg Met Ile
            180                 185                 190 ggc act gat gct ttt cag gag act cca att gtt gag gtg aca agg tct     624
Gly Thr Asp Ala Phe Gln Glu Thr Pro Ile Val Glu Val Thr Arg Ser
        195                 200                 205 att act aag cat aat tat tta gtt ttg gat gta gag gat att cct aga     672
Ile Thr Lys His Asn Tyr Leu Val Leu Asp Val Glu Asp Ile Pro Arg
210                 215                 220 att gtt aag gaa gcc ttt ttt tta gct aat tct ggt agg cct gga cct     720
Ile Val Lys Glu Ala Phe Phe Leu Ala Asn Ser Gly Arg Pro Gly Pro
225                 230                 235                 240
```

```
gtt ttg att gat ctt cct aaa gat att cag cag caa ttg gtt gtt cct    768
Val Leu Ile Asp Leu Pro Lys Asp Ile Gln Gln Gln Leu Val Val Pro
                245                 250                 255 gat tgg gat agg cct ttt aag ttg ggt ggg tat atg tct agg ctg cca    816
Asp Trp Asp Arg Pro Phe Lys Leu Gly Gly Tyr Met Ser Arg Leu Pro
                260                 265                 270 aag tcc aag ttt tcg acg aat gag gtt gga ctt ctt gag cag att gtg    864
Lys Ser Lys Phe Ser Thr Asn Glu Val Gly Leu Leu Glu Gln Ile Val
                275                 280                 285 agg ttg atg agt gag tcg aag aag cct gtc ttg tat gtg gga ggt ggg    912
Arg Leu Met Ser Glu Ser Lys Lys Pro Val Leu Tyr Val Gly Gly Gly
                290                 295                 300 tgt ttg aat tct agt gag gag ttg agg aga ttt gtt gag ttg aca ggg    960
Cys Leu Asn Ser Ser Glu Glu Leu Arg Arg Phe Val Glu Leu Thr Gly
305                 310                 315                 320 att ccg gtg gct agt act ttg atg ggg ttg ggg tct tac cct tgt aat   1008
Ile Pro Val Ala Ser Thr Leu Met Gly Leu Gly Ser Tyr Pro Cys Asn
                325                 330                 335 gat gaa ctg tct ctt cat atg ttg ggg atg cac ggg act gtt tat gcc   1056
Asp Glu Leu Ser Leu His Met Leu Gly Met His Gly Thr Val Tyr Ala
                340                 345                 350 aat tat gcg gtg gat aag gcg gat ttg ttg ctt gct ttc ggg gtt agg   1104
Asn Tyr Ala Val Asp Lys Ala Asp Leu Leu Leu Ala Phe Gly Val Arg
                355                 360                 365 ttt gat gat cgt gtg acc ggg aag ctc gag gcg ttt gct agc cgt gct   1152
Phe Asp Asp Arg Val Thr Gly Lys Leu Glu Ala Phe Ala Ser Arg Ala
370                 375                 380 aag att gtg cat att gat att gac tct gct gag att ggg aag aac aag   1200
Lys Ile Val His Ile Asp Ile Asp Ser Ala Glu Ile Gly Lys Asn Lys
385                 390                 395                 400 cag ccc cat gtg tcc att tgt gct gat gtt aaa ttg gca ttg cgg ggt   1248
Gln Pro His Val Ser Ile Cys Ala Asp Val Lys Leu Ala Leu Arg Gly
                405                 410                 415 atg aat aag att ctg gag tct aga ata ggg aag ctg aat ttg gat ttc   1296
Met Asn Lys Ile Leu Glu Ser Arg Ile Gly Lys Leu Asn Leu Asp Phe
                420                 425                 430 tcc aag tgg aga gaa gaa tta ggt gag cag aag aag gaa ttc cca ctg   1344
Ser Lys Trp Arg Glu Glu Leu Gly Glu Gln Lys Lys Glu Phe Pro Leu
                435                 440                 445 agt ttt aag aca ttt ggg gat gca att cct cca caa tat gcc att cag   1392
Ser Phe Lys Thr Phe Gly Asp Ala Ile Pro Pro Gln Tyr Ala Ile Gln
                450                 455                 460 gtg ctt gat gag ttg acc aat ggt aat gct att ata agt act ggt gtt   1440
Val Leu Asp Glu Leu Thr Asn Gly Asn Ala Ile Ile Ser Thr Gly Val
465                 470                 475                 480 ggg cag cac caa atg tgg gct gcg cag cat tac aag tac aga aac cct   1488
Gly Gln His Gln Met Trp Ala Ala Gln His Tyr Lys Tyr Arg Asn Pro
                485                 490                 495 cgc caa tgg ctg acc tct ggt ggg ttg ggg gct atg ggg ttt ggg cta   1536
Arg Gln Trp Leu Thr Ser Gly Gly Leu Gly Ala Met Gly Phe Gly Leu
                500                 505                 510 cca gcc gcc att gga gct gca gtt gct cga cca gat gca gtg gtt gtc   1584
Pro Ala Ala Ile Gly Ala Ala Val Ala Arg Pro Asp Ala Val Val Val
                515                 520                 525 gat att gat ggg gat ggc agt ttt att atg aat gtt caa gag ttg gct   1632
Asp Ile Asp Gly Asp Gly Ser Phe Ile Met Asn Val Gln Glu Leu Ala
                530                 535                 540 aca att agg gtg gaa aat ctc cca gtt aag ata atg ctg cta aac aat   1680
Thr Ile Arg Val Glu Asn Leu Pro Val Lys Ile Met Leu Leu Asn Asn
545                 550                 555                 560
```

```
caa cat tta ggt atg gtt gtc caa tgg gaa gat agg ttc tat aaa gct      1728
Gln His Leu Gly Met Val Val Gln Trp Glu Asp Arg Phe Tyr Lys Ala
            565                 570                 575 aac cgg gca cat aca tac ctt gga aac cct tcc aaa tct gct gat atc      1776
Asn Arg Ala His Thr Tyr Leu Gly Asn Pro Ser Lys Ser Ala Asp Ile
        580                 585                 590 ttc cct gat atg ctc aaa ttc gct gag gca tgt gat att cct tct gcc      1824
Phe Pro Asp Met Leu Lys Phe Ala Glu Ala Cys Asp Ile Pro Ser Ala
        595                 600                 605 cgt gtt agc aac gtg gct gat ttg agg gcc gcc att caa aca atg ttg      1872
Arg Val Ser Asn Val Ala Asp Leu Arg Ala Ala Ile Gln Thr Met Leu
        610                 615                 620 gat act cca ggg ccg tac ctg ctc gat gtg att gta ccg cat caa gag      1920
Asp Thr Pro Gly Pro Tyr Leu Leu Asp Val Ile Val Pro His Gln Glu
625                 630                 635                 640 cat gtg ttg cct atg att cca agt ggt gcc ggt ttc aag gat acc att      1968
His Val Leu Pro Met Ile Pro Ser Gly Ala Gly Phe Lys Asp Thr Ile
            645                 650                 655 aca gag ggt gat gga aga acc tct taa                                  1995
Thr Glu Gly Asp Gly Arg Thr Ser
            660
```

<210> SEQ ID NO 6
<211> LENGTH: 664
<212> TYPE: PRT
<213> ORGANISM: Beta vulgaris

<400> SEQUENCE: 6

```
Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
    130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Ser Arg Arg Met Ile
            180                 185                 190

Gly Thr Asp Ala Phe Gln Glu Thr Pro Ile Val Glu Val Thr Arg Ser
        195                 200                 205

Ile Thr Lys His Asn Tyr Leu Val Leu Asp Val Glu Asp Ile Pro Arg
    210                 215                 220
```

```
Ile Val Lys Glu Ala Phe Leu Ala Asn Ser Gly Arg Pro Gly Pro
225                 230                 235                 240

Val Leu Ile Asp Leu Pro Lys Asp Ile Gln Gln Gln Leu Val Val Pro
                245                 250                 255

Asp Trp Asp Arg Pro Phe Lys Leu Gly Gly Tyr Met Ser Arg Leu Pro
            260                 265                 270

Lys Ser Lys Phe Ser Thr Asn Glu Val Gly Leu Leu Glu Gln Ile Val
        275                 280                 285

Arg Leu Met Ser Glu Ser Lys Pro Val Leu Tyr Val Gly Gly Gly
290                 295                 300

Cys Leu Asn Ser Ser Glu Glu Leu Arg Arg Phe Val Glu Leu Thr Gly
305                 310                 315                 320

Ile Pro Val Ala Ser Thr Leu Met Gly Leu Gly Ser Tyr Pro Cys Asn
                325                 330                 335

Asp Glu Leu Ser Leu His Met Leu Gly Met His Gly Thr Val Tyr Ala
                340                 345                 350

Asn Tyr Ala Val Asp Lys Ala Asp Leu Leu Leu Ala Phe Gly Val Arg
            355                 360                 365

Phe Asp Asp Arg Val Thr Gly Lys Leu Glu Ala Phe Ala Ser Arg Ala
370                 375                 380

Lys Ile Val His Ile Asp Ile Asp Ser Ala Glu Ile Gly Lys Asn Lys
385                 390                 395                 400

Gln Pro His Val Ser Ile Cys Ala Asp Val Lys Leu Ala Leu Arg Gly
                405                 410                 415

Met Asn Lys Ile Leu Glu Ser Arg Ile Gly Lys Leu Asn Leu Asp Phe
            420                 425                 430

Ser Lys Trp Arg Glu Glu Leu Gly Glu Gln Lys Lys Glu Phe Pro Leu
        435                 440                 445

Ser Phe Lys Thr Phe Gly Asp Ala Ile Pro Pro Gln Tyr Ala Ile Gln
    450                 455                 460

Val Leu Asp Glu Leu Thr Asn Gly Asn Ala Ile Ile Ser Thr Gly Val
465                 470                 475                 480

Gly Gln His Gln Met Trp Ala Ala Gln His Tyr Lys Tyr Arg Asn Pro
                485                 490                 495

Arg Gln Trp Leu Thr Ser Gly Gly Leu Gly Ala Met Gly Phe Gly Leu
            500                 505                 510

Pro Ala Ala Ile Gly Ala Ala Val Ala Arg Pro Asp Ala Val Val Val
        515                 520                 525

Asp Ile Asp Gly Asp Gly Ser Phe Ile Met Asn Val Gln Glu Leu Ala
    530                 535                 540

Thr Ile Arg Val Glu Asn Leu Pro Val Lys Ile Met Leu Leu Asn Asn
545                 550                 555                 560

Gln His Leu Gly Met Val Val Gln Trp Glu Asp Arg Phe Tyr Lys Ala
                565                 570                 575

Asn Arg Ala His Thr Tyr Leu Gly Asn Pro Ser Lys Ser Ala Asp Ile
            580                 585                 590

Phe Pro Asp Met Leu Lys Phe Ala Glu Ala Cys Asp Ile Pro Ser Ala
        595                 600                 605

Arg Val Ser Asn Val Ala Asp Leu Arg Ala Ala Ile Gln Thr Met Leu
    610                 615                 620

Asp Thr Pro Gly Pro Tyr Leu Leu Asp Val Ile Val Pro His Gln Glu
625                 630                 635                 640

His Val Leu Pro Met Ile Pro Ser Gly Ala Gly Phe Lys Asp Thr Ile
```

Thr Glu Gly Asp Gly Arg Thr Ser
            660

<210> SEQ ID NO 7
<211> LENGTH: 1995
<212> TYPE: DNA
<213> ORGANISM: Beta vulgaris
<220> FEATURE:
<221> NAME/KEY: misc_feature
<222> LOCATION: (1)..(1994)
<223> OTHER INFORMATION: 4D6834 al2 WT
<220> FEATURE:
<221> NAME/KEY: CDS
<222> LOCATION: (1)..(1995)

<400> SEQUENCE: 7

```
atg gcg gct acc ttc aca aac cca aca ttt tcc cct tcc tca act caa      48
Met Ala Ala Thr Phe Thr Asn Pro Thr Phe Ser Pro Ser Ser Thr Gln
1               5                  10                  15 tta acc aaa acc cta aaa tcc caa tct tcc att tct tca acc ctc ccc      96
Leu Thr Lys Thr Leu Lys Ser Gln Ser Ser Ile Ser Ser Thr Leu Pro
            20                  25                  30 ttt tcc acc cct ccc aaa acc cca act cca ctc ttt cac cgt ccc ctc     144
Phe Ser Thr Pro Pro Lys Thr Pro Thr Pro Leu Phe His Arg Pro Leu
        35                  40                  45 caa atc tca tcc tcc caa tcc cac aaa tca tcc gcc att aaa aca caa     192
Gln Ile Ser Ser Ser Gln Ser His Lys Ser Ser Ala Ile Lys Thr Gln
    50                  55                  60 act caa gca cct tct tct cca gct att gaa gat tca tct ttc gtt tct     240
Thr Gln Ala Pro Ser Ser Pro Ala Ile Glu Asp Ser Ser Phe Val Ser
65                  70                  75                  80 cga ttt ggc cct gat gaa ccc aga aaa ggg tcc gat gtc ctc gtt gaa     288
Arg Phe Gly Pro Asp Glu Pro Arg Lys Gly Ser Asp Val Leu Val Glu
                85                  90                  95 gct ctt gag cgt gaa ggt gtt acc aat gtg ttt gct tac cct ggt ggt     336
Ala Leu Glu Arg Glu Gly Val Thr Asn Val Phe Ala Tyr Pro Gly Gly
            100                 105                 110 gca tct atg gaa atc cac caa gct ctg acg cgc tct aaa acc atc cgc     384
Ala Ser Met Glu Ile His Gln Ala Leu Thr Arg Ser Lys Thr Ile Arg
        115                 120                 125 aat gtc ctc ccc cgc cat gaa caa ggc ggg gtt ttc gcc gcc gag gga     432
Asn Val Leu Pro Arg His Glu Gln Gly Gly Val Phe Ala Ala Glu Gly
    130                 135                 140 tat gct aga gct act gga aag gtt ggt gtc tgc att gcg act tct ggt     480
Tyr Ala Arg Ala Thr Gly Lys Val Gly Val Cys Ile Ala Thr Ser Gly
145                 150                 155                 160 cct ggt gct acc aac ctc gta tca ggt ctt gct gac gct ctc ctt gat     528
Pro Gly Ala Thr Asn Leu Val Ser Gly Leu Ala Asp Ala Leu Leu Asp
                165                 170                 175 tct gtc cct ctt gtt gcc atc act ggc caa gtt cca cgc cgt atg att     576
Ser Val Pro Leu Val Ala Ile Thr Gly Gln Val Pro Arg Arg Met Ile
            180                 185                 190 ggc act gat gct ttt cag gag act cca att gtt gag gta aca agg tct     624
Gly Thr Asp Ala Phe Gln Glu Thr Pro Ile Val Glu Val Thr Arg Ser
        195                 200                 205 att act aag cat aat tat ttg gtt ttg gat gta gaa gat att cct aga     672
Ile Thr Lys His Asn Tyr Leu Val Leu Asp Val Glu Asp Ile Pro Arg
    210                 215                 220 att gtt aag gaa gcc ttt ttt tta gct aat tct ggc agg cct gga cct     720
Ile Val Lys Glu Ala Phe Phe Leu Ala Asn Ser Gly Arg Pro Gly Pro
225                 230                 235                 240
```

| | |
|---|---|
| gtt ttg att gat ctt cct aaa gat att cag cag caa ctg gtt gtt cct<br>Val Leu Ile Asp Leu Pro Lys Asp Ile Gln Gln Gln Leu Val Val Pro<br>245 250 255 | 768 |
| gat tgg gat agg cct ttt aag ttg ggt ggg tat atg tct agg ctg cca<br>Asp Trp Asp Arg Pro Phe Lys Leu Gly Gly Tyr Met Ser Arg Leu Pro<br>260 265 270 | 816 |
| aag tcc aag ttt tcg acg aat gag gtt gga ctt ctt gag cag att gtg<br>Lys Ser Lys Phe Ser Thr Asn Glu Val Gly Leu Leu Glu Gln Ile Val<br>275 280 285 | 864 |
| agg ttg atg agt gag tcg aag aag cct gtc ttg tat gtg gga ggt ggg<br>Arg Leu Met Ser Glu Ser Lys Lys Pro Val Leu Tyr Val Gly Gly Gly<br>290 295 300 | 912 |
| tgt ttg aat tct agt gag gag ttg agg aga ttt gtt gag ttg aca ggg<br>Cys Leu Asn Ser Ser Glu Glu Leu Arg Arg Phe Val Glu Leu Thr Gly<br>305 310 315 320 | 960 |
| att ccg gtg gct agt act ttg atg ggg ttg ggg tct tac cct tgt aat<br>Ile Pro Val Ala Ser Thr Leu Met Gly Leu Gly Ser Tyr Pro Cys Asn<br>325 330 335 | 1008 |
| gat gaa ctg tct ctt cat atg ttg ggg atg cac ggg act gtt tat gcc<br>Asp Glu Leu Ser Leu His Met Leu Gly Met His Gly Thr Val Tyr Ala<br>340 345 350 | 1056 |
| aat tat gcg gtg gat aag gcg gat ttg ttg ctt gct ttc ggg gtt agg<br>Asn Tyr Ala Val Asp Lys Ala Asp Leu Leu Leu Ala Phe Gly Val Arg<br>355 360 365 | 1104 |
| ttt gat gat cgt gtg act ggg aag ctc gag gcg ttt gct agc cgt gct<br>Phe Asp Asp Arg Val Thr Gly Lys Leu Glu Ala Phe Ala Ser Arg Ala<br>370 375 380 | 1152 |
| aag att gtg cat att gat att gac tct gct gag att ggg aag aac aag<br>Lys Ile Val His Ile Asp Ile Asp Ser Ala Glu Ile Gly Lys Asn Lys<br>385 390 395 400 | 1200 |
| cag ccc cat gtg tcc att tgt gct gat gtt aaa ttg gca ttg cgg ggt<br>Gln Pro His Val Ser Ile Cys Ala Asp Val Lys Leu Ala Leu Arg Gly<br>405 410 415 | 1248 |
| atg aat aag att ctg gag tct aga ata ggg aag ctg aat ttg gat ttc<br>Met Asn Lys Ile Leu Glu Ser Arg Ile Gly Lys Leu Asn Leu Asp Phe<br>420 425 430 | 1296 |
| tcc agg tgg aga gaa gaa tta ggt gag cag aag aag gaa ttc cca ctg<br>Ser Arg Trp Arg Glu Glu Leu Gly Glu Gln Lys Lys Glu Phe Pro Leu<br>435 440 445 | 1344 |
| agt ttt aag aca ttt ggg gat gca atc cct cca caa tat gcc att cag<br>Ser Phe Lys Thr Phe Gly Asp Ala Ile Pro Pro Gln Tyr Ala Ile Gln<br>450 455 460 | 1392 |
| gtg ctt gat gag ttg acc aat ggt aat gct att ata agt act ggt gtt<br>Val Leu Asp Glu Leu Thr Asn Gly Asn Ala Ile Ile Ser Thr Gly Val<br>465 470 475 480 | 1440 |
| ggg cag cac caa atg tgg gct gcg cag cat tac aag tac aga aac cct<br>Gly Gln His Gln Met Trp Ala Ala Gln His Tyr Lys Tyr Arg Asn Pro<br>485 490 495 | 1488 |
| cgc caa tgg ctg acc tct ggt ggg ttg ggg gct atg ggg ttt ggg cta<br>Arg Gln Trp Leu Thr Ser Gly Gly Leu Gly Ala Met Gly Phe Gly Leu<br>500 505 510 | 1536 |
| cca gcc gcc att gga gct gca gtt gct cga cca gat gca gtg gtt gtc<br>Pro Ala Ala Ile Gly Ala Ala Val Ala Arg Pro Asp Ala Val Val Val<br>515 520 525 | 1584 |
| gat att gat ggg gat ggc agt ttt att atg aat gtt caa gag ttg gct<br>Asp Ile Asp Gly Asp Gly Ser Phe Ile Met Asn Val Gln Glu Leu Ala<br>530 535 540 | 1632 |
| aca att agg gtg gaa aat ctc cca gtt aag ata atg ctg cta aac aat<br>Thr Ile Arg Val Glu Asn Leu Pro Val Lys Ile Met Leu Leu Asn Asn | 1680 |

```
545                 550                 555                 560
caa cat tta ggt atg gtt gtc caa tgg gaa gat agg ttc tat aaa gct    1728
Gln His Leu Gly Met Val Val Gln Trp Glu Asp Arg Phe Tyr Lys Ala
                565                 570                 575 aat cgg gca cat aca tac ctt gga aac cct tcc aaa tct gct gat atc    1776
Asn Arg Ala His Thr Tyr Leu Gly Asn Pro Ser Lys Ser Ala Asp Ile
                580                 585                 590 ttc cct gat atg ctc aaa ttc gct gag gca tgt gat att cct tct gcc    1824
Phe Pro Asp Met Leu Lys Phe Ala Glu Ala Cys Asp Ile Pro Ser Ala
                595                 600                 605 cgt gtt agc aac gtg gct gat ttg agg gcc gcc att caa aca atg ttg    1872
Arg Val Ser Asn Val Ala Asp Leu Arg Ala Ala Ile Gln Thr Met Leu
                610                 615                 620 gat act cca ggg ccg tac ctg ctc gat gtg att gta ccg cat caa gag    1920
Asp Thr Pro Gly Pro Tyr Leu Leu Asp Val Ile Val Pro His Gln Glu
625                 630                 635                 640 cat gtg ttg cct atg att cca agt ggt gcc ggt ttc aag gat acc att    1968
His Val Leu Pro Met Ile Pro Ser Gly Ala Gly Phe Lys Asp Thr Ile
                645                 650                 655 aca gag ggt gat gga aga acc tct taa                                1995
Thr Glu Gly Asp Gly Arg Thr Ser
                660

<210> SEQ ID NO 8
<211> LENGTH: 664
<212> TYPE: PRT
<213> ORGANISM: Beta vulgaris

<400> SEQUENCE: 8

Met Ala Ala Thr Phe Thr Asn Pro Thr Phe Ser Pro Ser Ser Thr Gln
1               5                   10                  15

Leu Thr Lys Thr Leu Lys Ser Gln Ser Ser Ile Ser Ser Thr Leu Pro
                20                  25                  30

Phe Ser Thr Pro Pro Lys Thr Pro Thr Pro Leu Phe His Arg Pro Leu
            35                  40                  45

Gln Ile Ser Ser Ser Gln Ser His Lys Ser Ser Ala Ile Lys Thr Gln
        50                  55                  60

Thr Gln Ala Pro Ser Ser Pro Ala Ile Glu Asp Ser Ser Phe Val Ser
65                  70                  75                  80

Arg Phe Gly Pro Asp Glu Pro Lys Gly Ser Asp Val Leu Val Glu
                85                  90                  95

Ala Leu Glu Arg Glu Gly Val Thr Asn Val Phe Ala Tyr Pro Gly Gly
                100                 105                 110

Ala Ser Met Glu Ile His Gln Ala Leu Thr Arg Ser Lys Thr Ile Arg
            115                 120                 125

Asn Val Leu Pro Arg His Glu Gln Gly Gly Val Phe Ala Ala Glu Gly
        130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Pro Arg Arg Met Ile
                180                 185                 190

Gly Thr Asp Ala Phe Gln Glu Thr Pro Ile Val Glu Val Thr Arg Ser
            195                 200                 205

Ile Thr Lys His Asn Tyr Leu Val Leu Asp Val Glu Asp Ile Pro Arg
        210                 215                 220
```

```
Ile Val Lys Glu Ala Phe Phe Leu Ala Asn Ser Gly Arg Pro Gly Pro
225                 230                 235                 240

Val Leu Ile Asp Leu Pro Lys Asp Ile Gln Gln Gln Leu Val Val Pro
                245                 250                 255

Asp Trp Asp Arg Pro Phe Lys Leu Gly Gly Tyr Met Ser Arg Leu Pro
                    260                 265                 270

Lys Ser Lys Phe Ser Thr Asn Glu Val Gly Leu Leu Glu Gln Ile Val
                275                 280                 285

Arg Leu Met Ser Glu Ser Lys Lys Pro Val Leu Tyr Val Gly Gly Gly
290                 295                 300

Cys Leu Asn Ser Ser Glu Glu Leu Arg Arg Phe Val Glu Leu Thr Gly
305                 310                 315                 320

Ile Pro Val Ala Ser Thr Leu Met Gly Leu Gly Ser Tyr Pro Cys Asn
                325                 330                 335

Asp Glu Leu Ser Leu His Met Leu Gly Met His Gly Thr Val Tyr Ala
                340                 345                 350

Asn Tyr Ala Val Asp Lys Ala Asp Leu Leu Leu Ala Phe Gly Val Arg
            355                 360                 365

Phe Asp Asp Arg Val Thr Gly Lys Leu Glu Ala Phe Ala Ser Arg Ala
370                 375                 380

Lys Ile Val His Ile Asp Ile Asp Ser Ala Glu Ile Gly Lys Asn Lys
385                 390                 395                 400

Gln Pro His Val Ser Ile Cys Ala Asp Val Lys Leu Ala Leu Arg Gly
                405                 410                 415

Met Asn Lys Ile Leu Glu Ser Arg Ile Gly Lys Leu Asn Leu Asp Phe
                420                 425                 430

Ser Arg Trp Arg Glu Glu Leu Gly Glu Gln Lys Lys Glu Phe Pro Leu
                435                 440                 445

Ser Phe Lys Thr Phe Gly Asp Ala Ile Pro Pro Gln Tyr Ala Ile Gln
            450                 455                 460

Val Leu Asp Glu Leu Thr Asn Gly Asn Ala Ile Ile Ser Thr Gly Val
465                 470                 475                 480

Gly Gln His Gln Met Trp Ala Ala Gln His Tyr Lys Tyr Arg Asn Pro
                485                 490                 495

Arg Gln Trp Leu Thr Ser Gly Gly Leu Gly Ala Met Gly Phe Gly Leu
                500                 505                 510

Pro Ala Ala Ile Gly Ala Ala Val Ala Arg Pro Asp Ala Val Val Val
                515                 520                 525

Asp Ile Asp Gly Asp Gly Ser Phe Ile Met Asn Val Gln Glu Leu Ala
                530                 535                 540

Thr Ile Arg Val Glu Asn Leu Pro Val Lys Ile Met Leu Leu Asn Asn
545                 550                 555                 560

Gln His Leu Gly Met Val Val Gln Trp Glu Asp Arg Phe Tyr Lys Ala
                565                 570                 575

Asn Arg Ala His Thr Tyr Leu Gly Asn Pro Ser Lys Ser Ala Asp Ile
                580                 585                 590

Phe Pro Asp Met Leu Lys Phe Ala Glu Ala Cys Asp Ile Pro Ser Ala
                595                 600                 605
```

```
Arg Val Ser Asn Val Ala Asp Leu Arg Ala Ala Ile Gln Thr Met Leu
    610             615                 620

Asp Thr Pro Gly Pro Tyr Leu Leu Asp Val Ile Val Pro His Gln Glu
625             630                 635                 640

His Val Leu Pro Met Ile Pro Ser Gly Ala Gly Phe Lys Asp Thr Ile
                645             650                 655

Thr Glu Gly Asp Gly Arg Thr Ser
            660
```